United States Patent [19]
Hubbard et al.

[11] Patent Number: 6,011,992
[45] Date of Patent: Jan. 4, 2000

[54] SYSTEM FOR MEASURING AND INDICATING CHANGES IN THE RESISTANCE OF A LIVING BODY

[75] Inventors: Lafayette Ron Hubbard, deceased, late of Sussex, United Kingdom; by Norman F. Starkey, legal representative, Los Angeles, Calif.; John McCormick, Perris, Calif.; James Stavropoulos, Redondo Beach, Calif.; Richard Stinnett, Corona, Calif.

[73] Assignee: Church of Spirtual Technology, Los Angeles, Calif.

[21] Appl. No.: 08/647,414

[22] Filed: May 9, 1996

[51] Int. Cl.$^7$ ........................................ A61B 5/05
[52] U.S. Cl. ........................................ 600/547; 600/535
[58] Field of Search ........................... 600/535, 547

[56] References Cited

U.S. PATENT DOCUMENTS

| | | | |
|---|---|---|---|
| 3,991,746 | 11/1976 | Hanna | 600/535 |
| 4,300,579 | 11/1981 | Briggs | 600/547 |
| 4,459,995 | 7/1984 | Conners et al. | 600/547 |
| 4,578,635 | 3/1986 | Mee et al. | 324/692 |

*Primary Examiner*—Cary O'Connor
*Assistant Examiner*—Pamela L. Wingood
*Attorney, Agent, or Firm*—Small Larkin, LLP

[57] ABSTRACT

A system for measuring changes in the resistance of a living body includes a resistance measuring circuit, an amplifier circuit and an indicator circuit in which the amplifier circuit includes a calibration circuit to give a generally constant amplitude response to a given measured input. Radio frequency insulators are included to reduce noise in the system. The circuits are operated such that when an overall change in the resistance of a living body occurs, the resistance measuring circuit is adjusted to determine the overall resistance. To account for changes in sensitivity caused by the overall change in resistance, the gain of the amplifier circuit is automatically adjusted to thereby maintain a generally constant amplitude response.

22 Claims, 18 Drawing Sheets

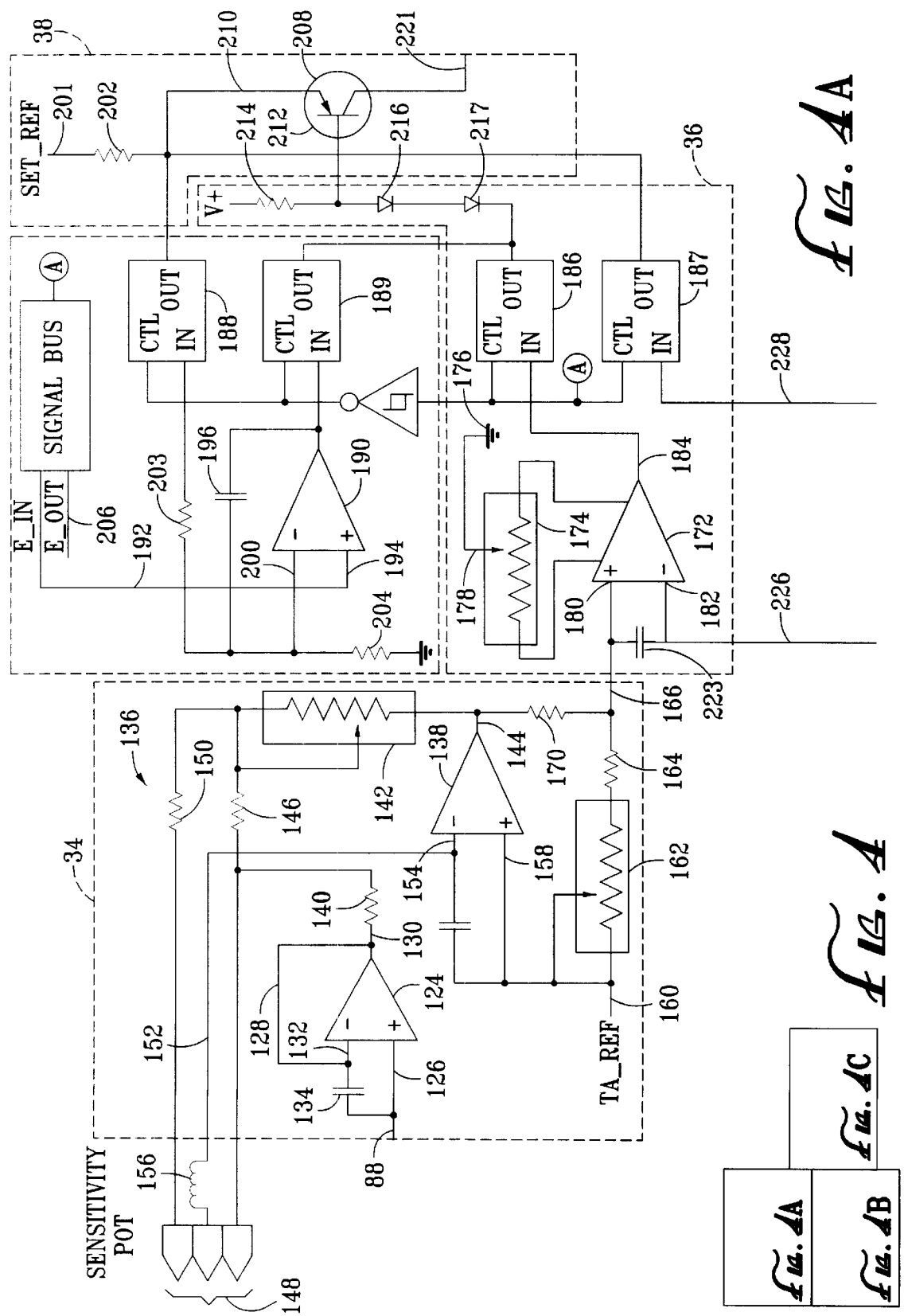

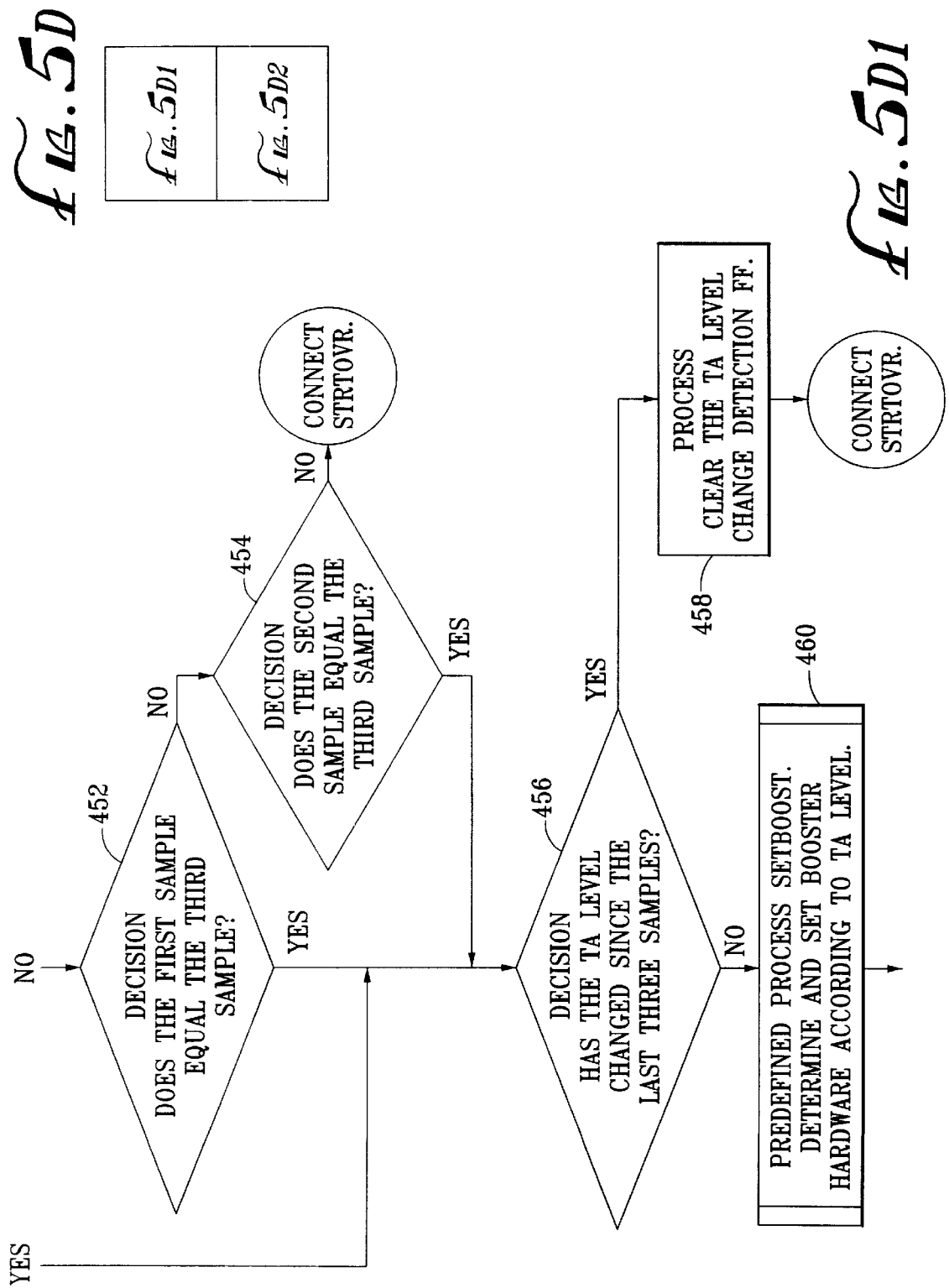

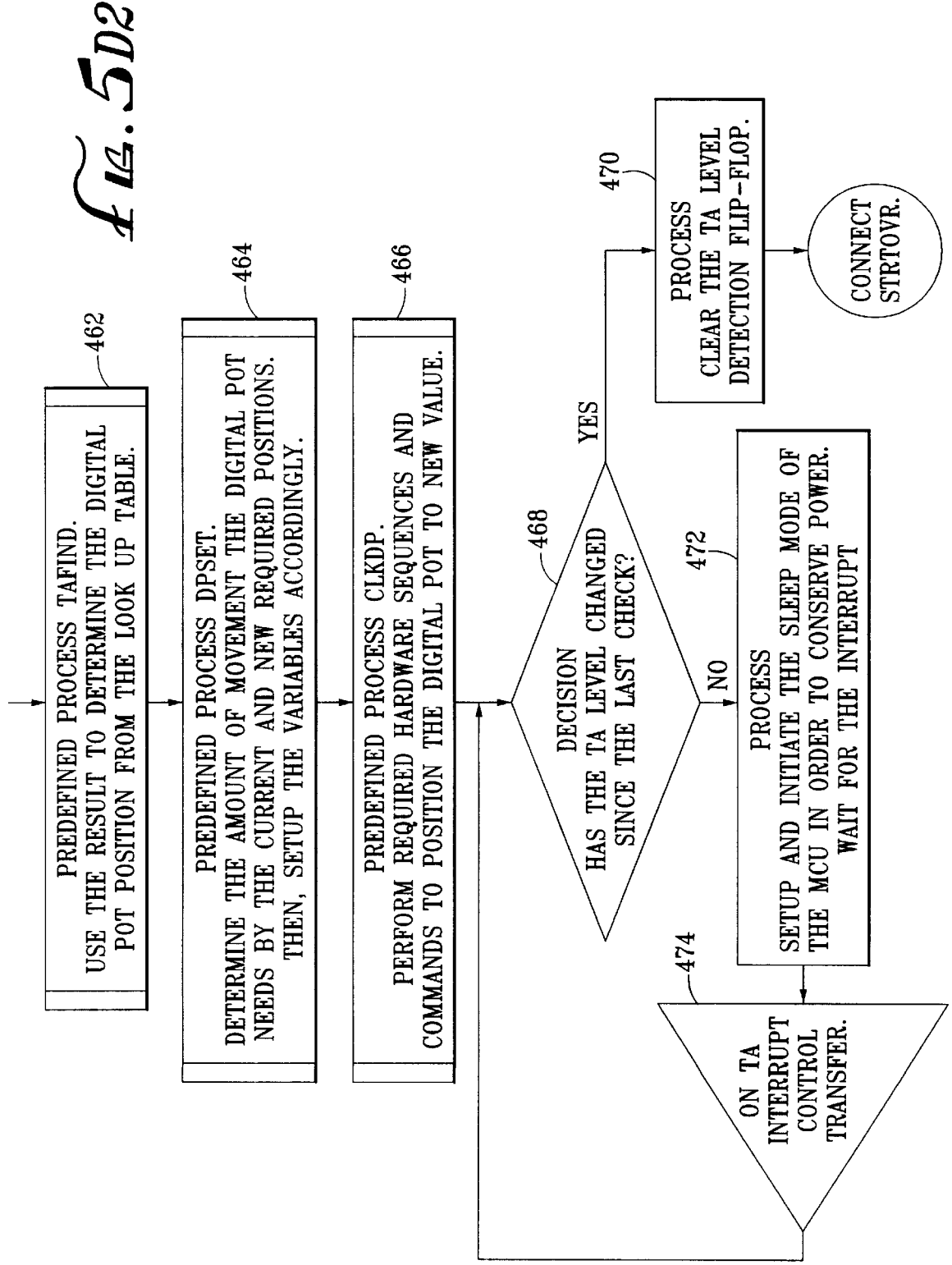
Fig. 5D2

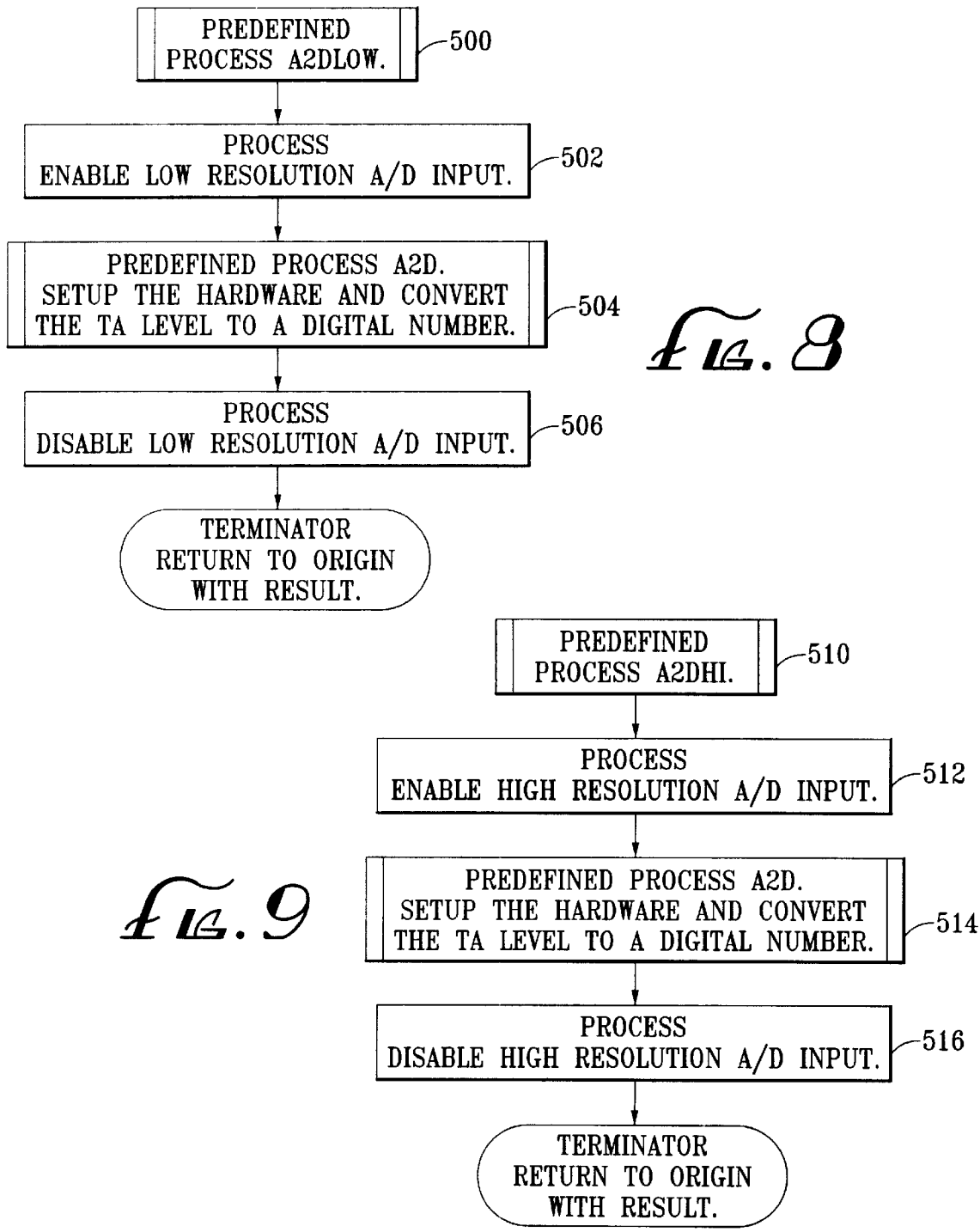

SYSTEM FOR MEASURING AND INDICATING CHANGES IN THE RESISTANCE OF A LIVING BODY

BACKGROUND OF THE INVENTION

1. Field of the Invention

This invention relates to an improved device for indicating and measuring variations in the resistance of a living body.

2. Prior Art

With the advent of Lafayette R. Hubbard's device for measuring and indicating changes in a living body, the capability of discerning small changes in the resistance of living body through electromechanical measurement was made available. That device includes, generally, a resistance measuring circuit, an amplifier circuit and an indicator circuit. Although adequately suited for its intended purpose of detecting changes in the resistance of a living body, it was not able to accurately indicate the measured changes. Various improvements have attempted to overcome this problem, described and illustrated in U.S. Pat. No. 3,290,589 and U.S. Pat. No. 4,459,995. Such devices operate to generate a signal representative of small measurements in the resistance of a living body. This is then amplified into a signal that is discernable and useful on an indicator perceptible to a human being, such as a visual display. One problem with these devices is that undesirable characteristics in the signal may mask or falsely report small measurements. These undesirable characteristics may be caused by radio-frequency interference and/or internal non-linearities in the device itself. Thus, a need exists for a device that can more accurately indicate changes in the resistance of living body.

SUMMARY OF THE PRESENT INVENTION

It is a general object of the present invention to accurately indicate small changes in the resistance of a living body.

It is a specific object of the present invention to eliminate undesirable characteristics in the signal representative of the resistance of a living body.

It is a feature of the present invention to include an active calibration circuit to give a generally constant amplitude response to a given measured input.

It is an advantage of the present invention that the sensitivity of the device is maintained at a constant level.

In accordance with the objects, features and advantages of the present invention, an improved electrical resistance measuring or indicating device comprising a resistance measuring circuit having input leads connected to a living body for producing measurement signals representative of the resistance of a living body is provided. An amplifier circuit receives the measurement signals and amplifies them to a perceptible level. An indicator circuit receives the amplified signals and provides the measurement signals in a perceptible form. The present invention advantageously includes passive and active devices to eliminate undesirable characteristics in the measurement signal.

One feature of the present invention is an active calibration circuit. The calibration circuit functions to give a generally constant amplitude response in the indicator circuit to a given change in resistance from the resistance measuring circuit. In the preferred embodiment of the calibration circuit, a feedback circuit portion and a control circuit portion cooperatively monitor operation of the device and anticipate variations in amplitude response in the indicator circuit. A compensator is also included to adapt or calibrate the amplifier circuit to account for the anticipated amplitude variations.

BRIEF DESCRIPTION OF THE DRAWINGS

Other objects and advantages of the invention will become apparent from the following detailed description taken in connection with the accompanying drawings, in which:

FIG. 3 is a functional block diagram of a preferred resistance measuring circuit of the present invention;

FIG. 4A is a functional block diagram of a preferred amplifier circuit of the present invention;

FIGS. 5A–5D represent a flow diagram of a main software routine;

FIG. 8 represents a flow diagram of an analog-to-digital low resolution routine;

FIG. 9 represents a flow diagram of an analog-to-digital high resolution routine;

DETAILED DESCRIPTION OF THE INVENTION AND PREFERRED EMBODIMENTS

Figure 1:
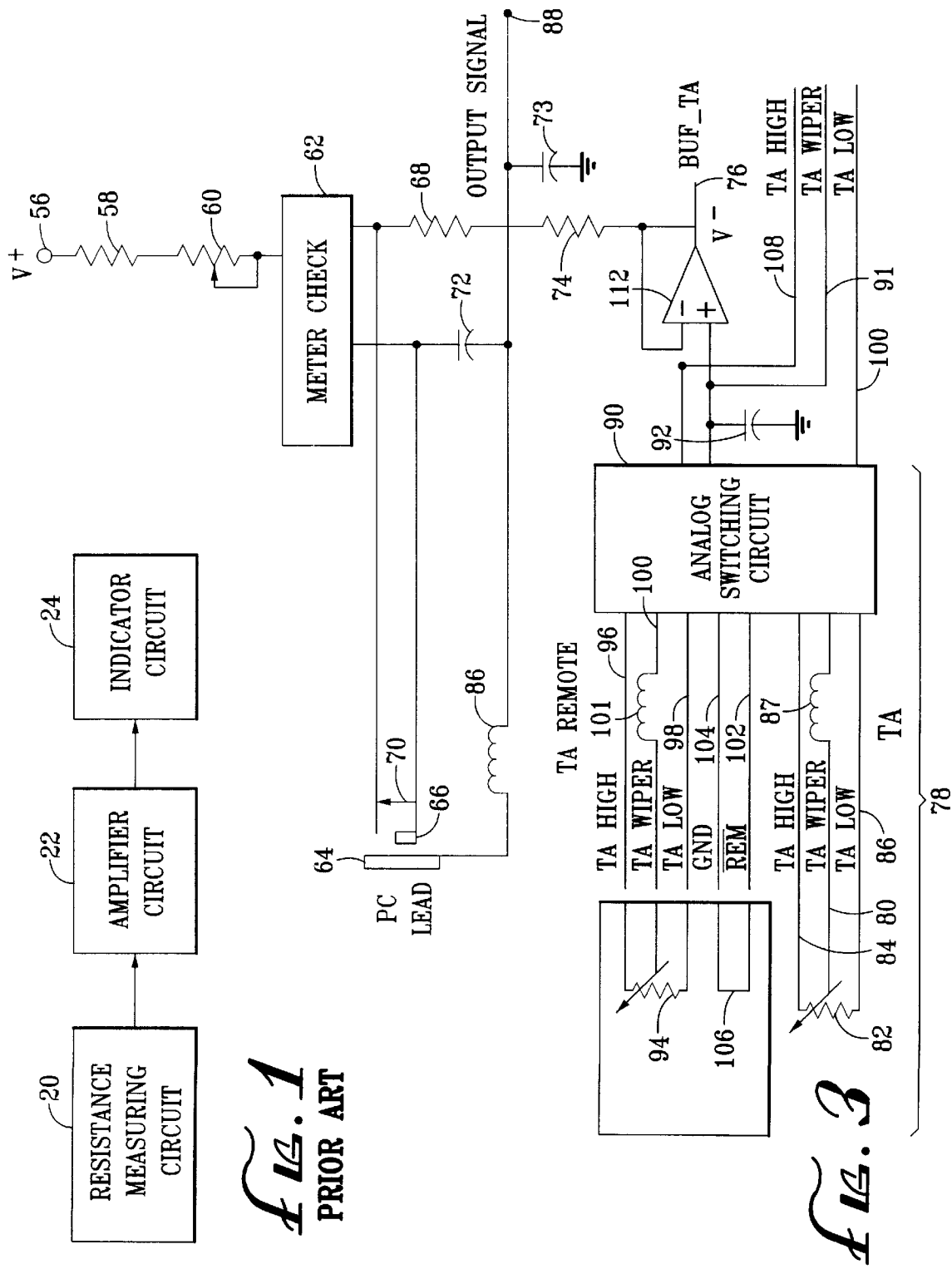
FIG. 1 is a functional block diagram of a conventional device for measuring the resistance of a living body.

Referring to the figures for purposes of illustration, the present invention may be used in combination with any conventional three stage circuits for measuring and indicating changes in the resistance of a living body. With reference to FIG. 1, such devices typically use a resistance measuring circuit 20 to transform measured resistances across a living body in the form of a measurement signal. The resistance measuring circuit connects to the amplifier circuit 22 that amplifies the measured signal to a perceptible level. An indicator circuit 24 connected to the amplifier circuit 22 produces the measured signal in a perceptible form. The resistance measuring circuit 20 may accomplish such measurements using a bridge or voltage divider circuit of the type conventional for measuring the resistance of a living body. A three stage circuit incorporating a bridge circuit of the type suitable for this purpose is disclosed in U.S. Pat. No. 4,702,259, U.S. Pat. No. 4,459,995 and U.S. Pat. No. 3,290,589, each of which is incorporated herein by reference. A three stage circuit incorporating a voltage divider circuit of the type suitable for this purpose is incorporated in the "HUBBARD™ PROFESSIONAL MARK SUPER VII" device manufactured and sold by Hubbard Electrometer Manufacturing of Los Angeles, Calif.

Based upon the above mentioned, known combinations the realization was made that the circuit required means for automatically increasing sensitivity for high resistance levels and automatic adjustment for low resistance levels. This improvement provides for a constant amplitude response in the indicator circuit 24.

Figure 2:
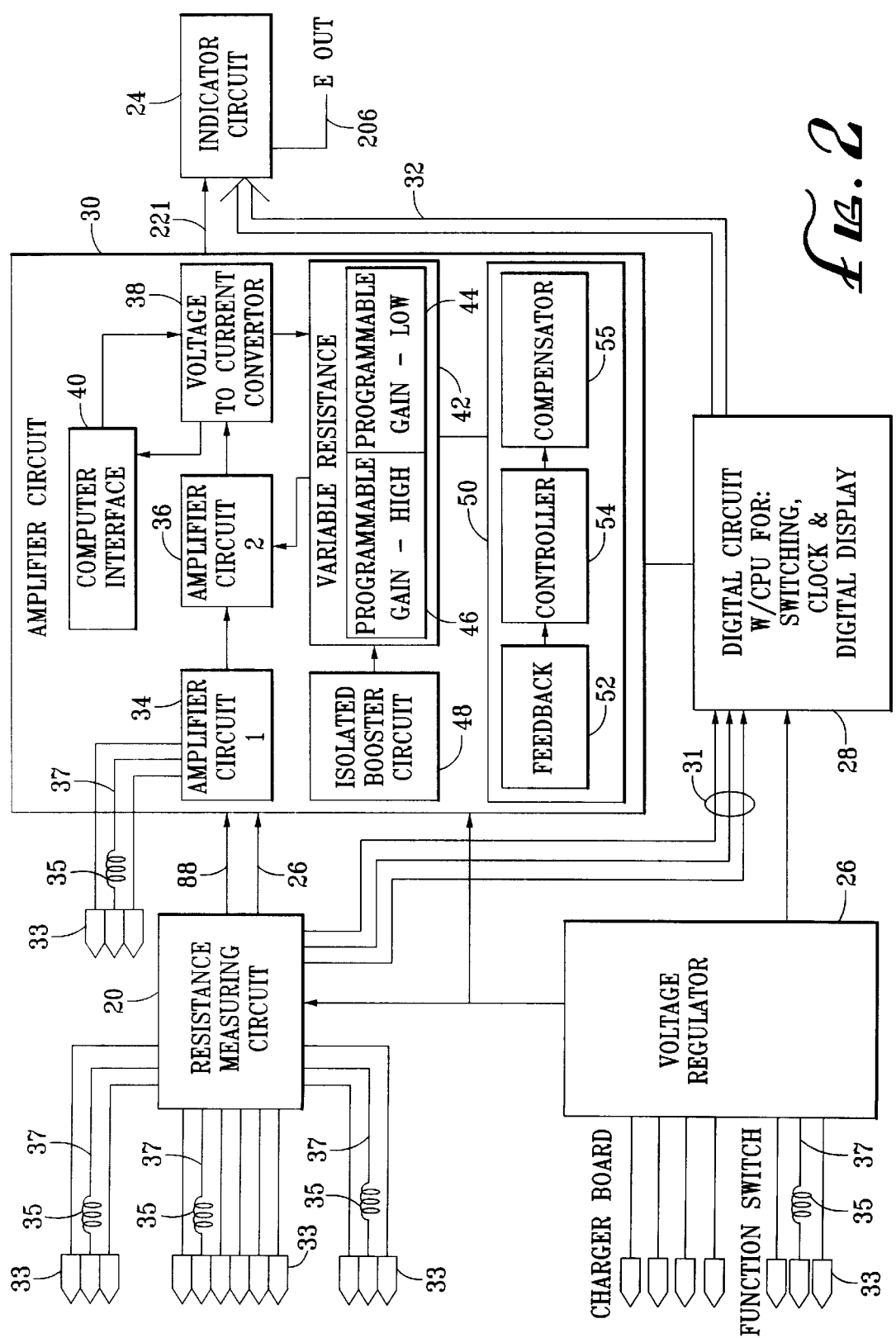
FIG. 2 is a functional block diagram of a device of the present invention.

The presently preferred embodiment, illustrated in functional block diagram form in FIG. 2, incorporates the inventive features within a conventional Hubbard Professional Mark Super VII™ circuit. Such a circuit additionally uses a voltage regulator 26 to establish stable, direct-current voltage levels throughout the electrical circuit. A digital circuit 28, controlled by a microprocessor (these conventional components are not shown), is used for tracking signals provided by leads 31 from the resistance measuring circuit 20, maintaining a date and time display and maintaining various conventional switching functions. Display leads 32 provide clock and signal tracking signals to conventional liquid crystal and code LCD displays which are located in the indicator circuit 24. The digital circuit may also be of the type disclosed in U.S. Pat. No. 4,702,259. Other leads 33 extend from the voltage regulator circuit 26, the resistance measuring circuit 20 and the amplifier circuit 30 and connect conventionally to various conventional manual controls (not shown). These leads may intercept radio signals thereby causing radio frequency (RF) interference. In the preferred embodiment of the present invention, the circuit board includes inductors 35 extending from the wiper leads 37 of the manual controls. Such manual controls may include a function switch, a low voltage potentiometer, a remote low voltage potentiometer, a trim variable resistor and a sensitivity control.

In accordance with the present invention, the amplifier circuit 30 includes generally two amplifier stages. A first amplifier circuit 34 for receiving and logarithmically amplifying the measured signal. A second amplifier circuit 36 is connected to the output of the first amplifier circuit 34 and functions to customize and amplify the gain of the measured signal. A computer interface 40, optionally, provides input to the voltage to current convertor circuit 38 for uses where a simulated measured signal is desired. A voltage to current convertor circuit 38 connected to the output of the second amplifier circuit 36 and functions to modify the measured signal into a form usable by the indicator circuit 24 and provides the modified signal to the circuit 24 through lead 221. The voltage to current convertor circuit 38 also provides feedback to the second amplifier and computer interface 40. A variable resistance circuit 42 connects to the second amplifier circuit 36 and provides an amplifier feedback signal to amplify the measured signal from the resistance measuring circuit 20. The variable resistance circuit 42 includes high and low programmable gain segments 46 and 44. An isolated booster switching circuit 48 connects to the variable resistance circuit 42 for a manual gain adjustment. Also connected to the variable resistance circuit 42 is the calibration circuit 50. The calibration circuit 50 functions as a calibration means to adjust the output of the amplifier circuit. In the presently preferred embodiment, the calibration circuit 50 includes a feedback circuit 52, a controller circuit 54 and a compensator circuit 55.

The resistance measuring circuit of the preferred embodiment (FIG. 3) is of the voltage divider type. In a voltage divider circuit, a high voltage potential 56 connects in series with a first voltage dividing resistor 58. The first resistance may use a variable resistor 60 to trim or offset the first resistance value. A conventional meter check switch 62 either manually selected or under the control of the digital circuit 28 optionally switches the path of the voltage divider circuit between a pair of external lead 66 and lead 64 for connection to a living body and a 5K ohm resistor 68 that operates as a check resistance in place of a living body. The conventional electrodes intended to connect to a living body attach via a plug (not shown). When the plug is physically inserted the external leads 64 and 66 are intended to be connected with a living body. When the plug is removed, a second switch 70 connects the high potential lead 66 to the 5K ohm resistor 68. Additionally, a capacitor 72 connects between the external leads 64 and 66 in series with an inductor 86. The inductor 86 and capacitor 72 function to reduce signal interference. The second voltage dividing resistance 68 is formed by the skohm resistor 68 or by the resistance defining body between the meter check switch 62 and an output lead 88. A third voltage dividing resistance 74 connects in series between the output lead 88 and a low voltage potential 76.

The low voltage potential value is manually adjustable using a manual adjustment device 78. Preferably, the manual adjustment device 78 includes a wiper lead 80 from a potentiometer 82 connected between a high and low voltage. The wiper lead 80 circuit includes an inductor 87 normally connected in series through an analog switching circuit 90 to lead 91. Inductor 87 is also connected to a capacitor 92 [connecting to ground] and they function to minimize interference. The manual adjustment device 78 may normally be a built-in potentiometer 82 or an external potentiometer 94. The external potentiometer 94 also connects across high and low voltage leads 96 and 98 and a wiper lead 100 to the analog switching circuit.

The external variable resistor 94 also includes a remote [$\overline{REM}$] signal lead 102 and a ground lead 104. The analog switching circuit 90 which may, conventionally, include a manual switch or a voltage divider and latches connected to an analog switch (not shown), the switching circuit 90 selectively actuates the internal potentiometer 82 or the external potentiometer. In the second case, selection of the potentiometer 94 is made according to the voltage state of the $\overline{REM}$ signal lead 102. The signal is maintained "high" when using the internal potentiometer 82 and is connected to ground 104 by a lead 106 in the external potentiometer 94. The voltage values of the wiper 91, high voltage value 108 and low voltage value 100 from the potentiometer in use are sent to the digital circuit 28 (FIG. 2) to compute the digital potentiometer signal readings. The wiper output lead 91 is sent through a signal buffer 112 comprising a voltage follower to prevent current loss in the low voltage potential 76.

Referring to the illustration of FIGS. 4A, B and C, the first amplifier circuit 34 receives the measured signal provided by the resistance measuring circuit signal output lead 88. The first amplifier circuit 34 includes an operational amplifier (op-amp) 124 having a positive input 126 connected to the signal output lead 88 from the resistance measurement circuit 20 (FIG. 1). The op-amp 124 is configured as a voltage follower with a feedback lead 128 extending from the op-amp output lead 130 to the negative input 132. A capacitor 134 connects between the positive and negative inputs 126 and 132 of the op-amp 124 to help attenuate RF interference in the measured signal. The op-amp output lead 130 in parallel with a feedback loop 136 provides the negative input to an op-amp 138, which functions as the first stage amplifier. A resistor 140 connects in series, at one end, to the output 130 of the voltage follower unfiltered op-amp 124. The other end of the series connection of resistor 140 is to a preset potentiometer 142 and to the output lead 144 of the first stage amplifier through two parallel resistive branches. The first branch includes a resistor 146 connected between the preset potentiometer 142 and the first resistor 140. The second branch includes a conventional user adjustable potentiometer connecting at electrodes 148 connected in series with a resistor 150 and the preset variable resistor 142. The user adjustable potentiometer (not shown) functions as a sensitivity pot. The sensitivity pot electrodes 148 are connected to the negative input lead 154 of the first stage amplifier through an inductor and a wiper lead 152, 156. The positive input lead 158 for the first stage op-amp receives a voltage reference signal 160 from the voltage regulator 26 providing a steady reference of 5.25 volts. The voltage reference lead 160 also connects with a resistive feedback branch which includes a second preset variable resistor 162 and fixed resistor 164 connected to the output lead 166 of the first amplifier circuit. The output 144 of the first stage amplifier also connects to the output lead 166 through a fixed resistor 170. Those skilled in the art will appreciate that the configuration of this first stage amplifier circuit provides an attenuated summing amplifier that sums together the value of the signal output lead 88 from the resistance measuring circuit 20 amplified by the gain of operational amplifier 138 and the value of the voltage reference 160. The operational amplifiers 124 and 138 of the first stage circuit are of the type model OP420 manufactured by Analog Devices, Inc. of Norwood, Mass. The output lead 166 of this summed, amplified signal connects to the second stage amplifier circuit 36. The first amplifier circuit also varies the gain of the instrument from 1 to 10 logarithmically as the variable resistor 142 is changed from a low to high resistance value.

In the second stage amplifier circuit 36, an operational amplifier 172 of the type Model OP90 manufactured by Analog Devices, Inc. is included with a variable resistance feedback branch. This particular type of amplifier requires offset compensation using a variable resistor 174 connected to ground 176 via a wiper 178. Other types of amplifiers suitable for this purpose may not require such a circuit. The output lead 166 of the first stage amplifier circuit 34 is connected to the positive input lead 180 of the second stage op-amp 172. A variable resistance circuit 42 provides a gain feedback to the negative input lead 182 of the second amplifier 172. The output lead 184 of the second stage amplifier 172 connects to one gate 186 of a plurality of latched gates 186–187. These gates selectively connect the voltage to current converter 38 to the second stage circuit 36 and the computer interface 40. The switching is accomplished by the digital circuit 28 in response to the selection by the operator in a conventional manner.

The computer interface 40 connects through the latching gates 188 and 189 to the voltage to current circuit 38. The computer interface 40 includes an amplifier 190 similar to the second stage circuit with an E-IN signal lead 192 extending from the signal bus and connecting to the positive input lead 194 of the amplifier. A first capacitor 196 provides filtered feedback and connects between the negative input lead and the output of the amplifier 190. The negative input lead further connects to a voltage divider feedback circuit including a voltage reference 201, two pull-up resistors 202 and 203, a latch gate 188, and a third resistor 204 connected to ground. The computer interface E IN lead 192 receives a playback signal or emulated playback signal of a previously recorded session and duplicates the output on the indicator circuit using the amplifier 190 of the computer interface. A signal lead E_OUT 206 receives signals indicating changes in the resistance of a living body from the indicator circuit 24 and transmits the measured signals to the computer interface 40.

The voltage to current convertor circuit 38 includes a transistor 208 having an emitter lead 210 connected to the "high" voltage level 201 via bias resistor 202 and the latch gates 187 and 188. The base lead 212 connects to a "high" voltage via a pull-up resistor 214 and two series diodes 216–217 reverse biased in relation to the base lead 212. The diodes 216–217 connect through latches 186 and 189 to the output of the second stage amplifier 172 and the computer interface amplifier output lead respectively. The collector lead of the transistor forms the output lead 221 connecting to the indicator circuit 24.

Figure 4B:
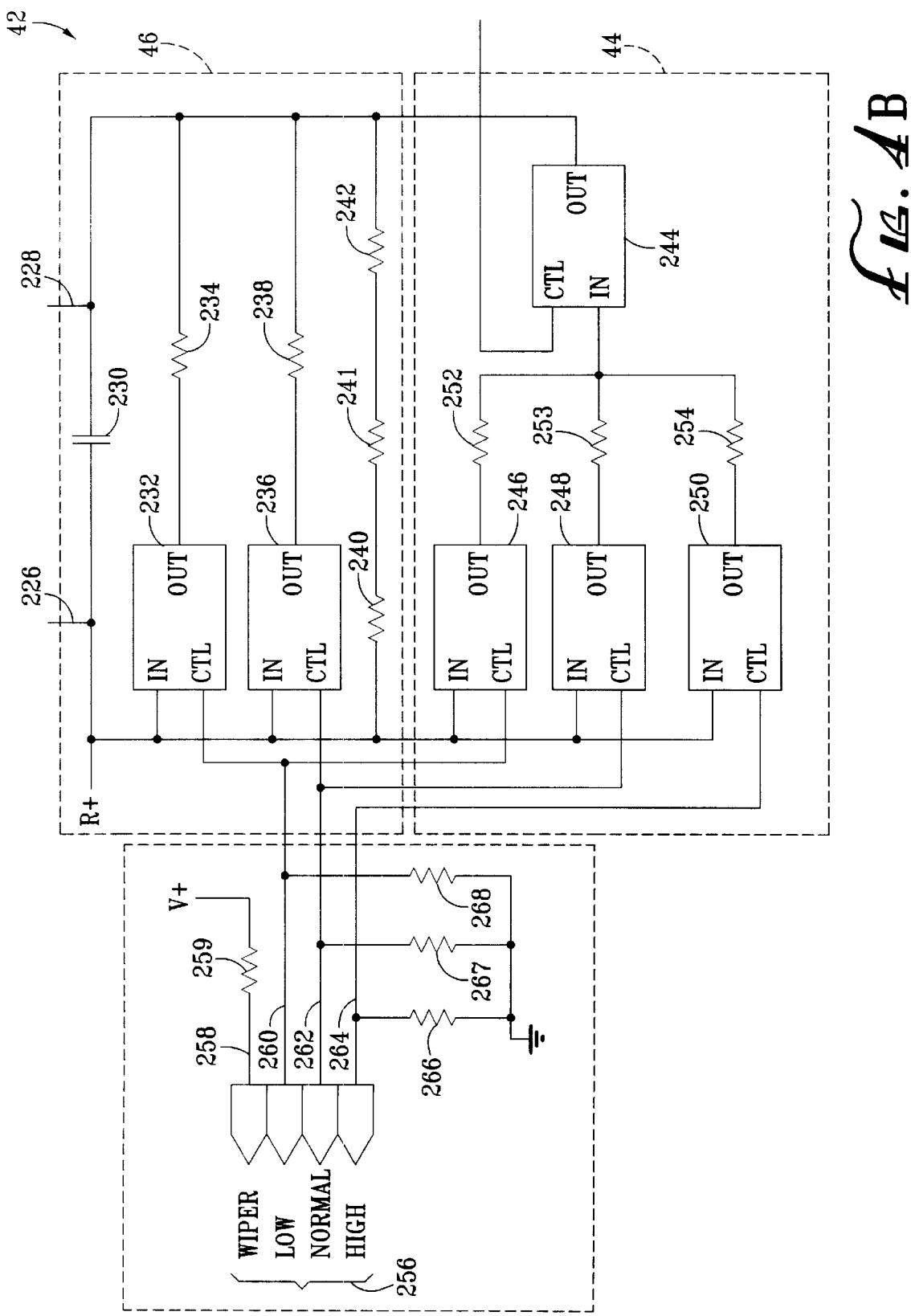
FIG. 4B is a functional block diagram of a variable resistance circuit and booster circuit.

The variable resistance circuit 42 (FIG. 4B) includes a programmable gain low circuit 44 and a programmable gain high circuit 46. Changes in the low voltage potential 76 from the resistance measuring circuit (FIG. 3) dictates which of these variable resistance circuits will be used to provide variable gain as will be described below. Referring to FIGS. 4A and 4B, the variable resistance circuit 42 connects through lead 226, 228. Circuit 42 connects through lead 228 to the negative input lead 182 of the op-amp 172 to the voltage to current converter 38 through latch gate 187 and to the voltage supply 201 through a resistor 202. A capacitor 223 (FIG. 4A) extends between the positive input lead 180 and the negative input lead 182, to provide further attenuation of the RF interference signals. The programmable gain high circuit 46 includes four circuit segments connected in parallel between the two leads 226 and 228 of the variable resistance circuit. A first segment includes a capacitor 230. The second segment includes a latched gate 232 and a resistor 234. The third segment includes a latched gate 236 and a resistor 238. The fourth segment includes three resistors 240–242 connected in series. The two latched gates 232 and 236 are controlled by the isolated booster switch circuit 48 (FIG. 2). The programmable gain low circuit 44 includes a separate latched gate 244 connected to the calibration circuit 50, see FIG. 4B discussed in detail below, and includes three branches connected in parallel. Each branch of the programmable gain low portion includes a separate latched gate 246, 248 and 250 connected in series with respective resistors 252, 253 and 254 selectively connected in circuit depending upon the setting of the isolated booster switching circuit 48 (FIG. 2).

The booster switch circuit 48 includes a switch 256 with a wiper 258 capable of three separate low 260, normal 262 and high 264 settings. The leads 260, 262 and 264 are all connected to ground through respective pull-down resistors 268, 267 and 266 respectively. The gates to which each of these respective leads are attached, are closed when the ground voltage is detected. The wiper 258 of the switch 256 includes a positive or high voltage level. When the wiper connects with either the high 264, normal 262 or low 260 circuit, the connected lead is drawn to a high voltage level. The latch gate connected to the respective lead will open the latched circuit when detecting the high voltage. The programmable gain high circuit is always on, even in programmable gain low mode. The input signal from the first stage amplifier circuit 34 is further amplified according to the low, normal and high settings of the booster switch 256 which changes the gain of the op-amp on a linear by 10 scale. The second stage op amp 172 provides additional gain by way of the booster switch 256 such that the gain is multiplied by 1 in the low booster position, by 10 in the NORMAL booster position and by 100 in the HIGH booster position. In addition the second stage op amp 172 provides gain ranging from 0.7x to 50x which is entirely under the control of MCU 334, described in greater detail below. Because the micro-controlled gain is independent of the sensitivity and booster, it may be thought of as a third stage. Each of these three stages are factored into the overall gain of the circuit such that the output gain is the product of the three stages. The lowest possible gain is 1.0×1.0×0.7=0.7 and the highest possible gain is 10×100×50=50,000.

Figure 4C:
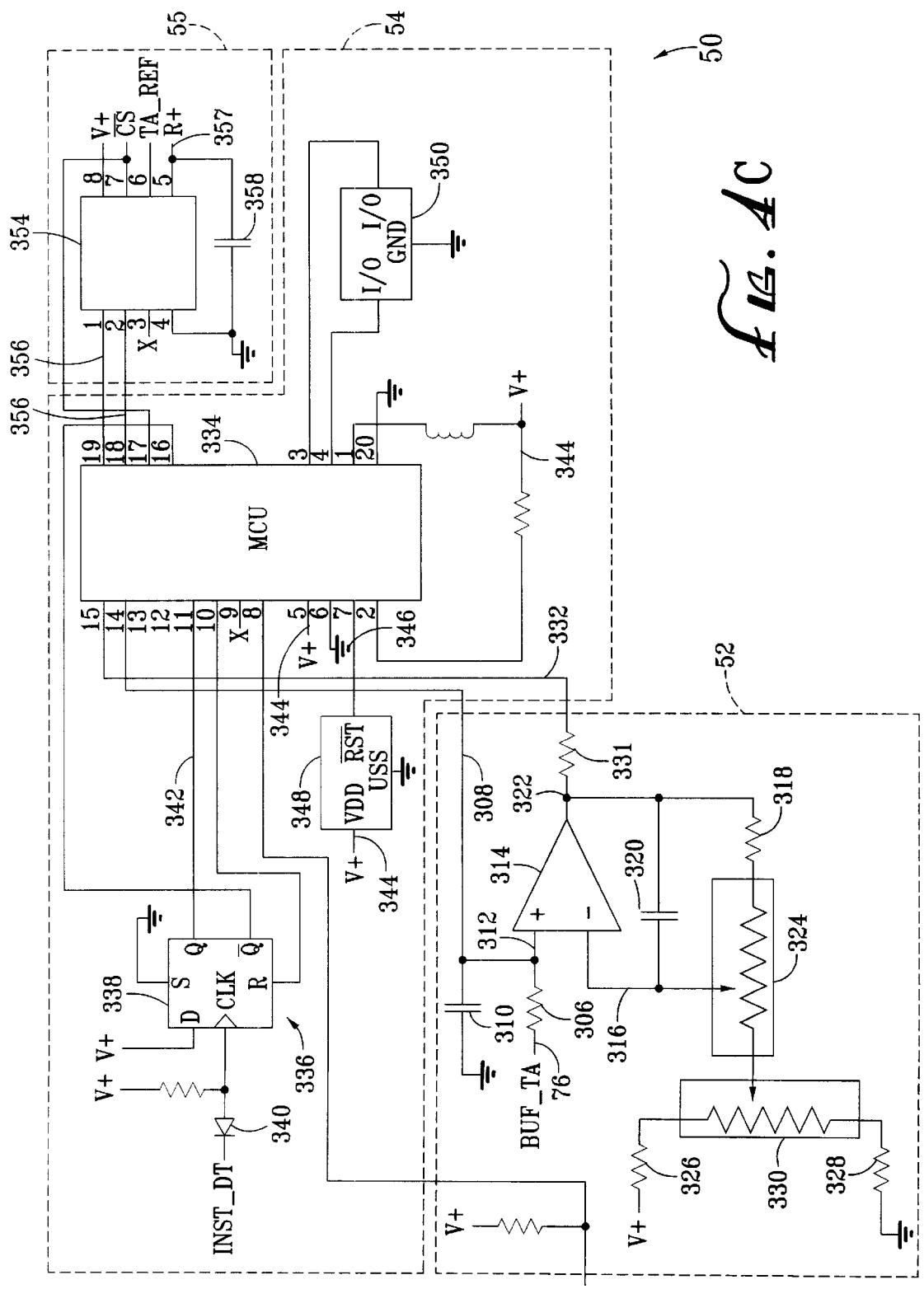
FIG. 4C is a functional block diagram of a feedback and control circuit.

The control and feedback circuit 50 (FIG. 4C) provides active calibration of the amplifier in response to changes or movement in the manual adjustment device 78 of the resistance measuring circuit 20. The control and feedback circuit 50 connects to the variable resistance circuit at the negative input lead 182 of the op-amp as illustrated by lead 356 (FIG. 4C) connecting in series to lead 226 (FIG. 4B) and op amp 172 negative input 182 and the control and feedback circuit 50 connects at the control latch lead 272 (FIGS. 4b and 4c) of the programmable gain low/high latch gate 244. The control and feedback circuit 50 may be used to provide active calibration in response to any changes in the circuit that may cause an undesirable characteristic in the measured signal. In the presently preferred embodiment the control and feedback circuit monitors and reacts to changes in the manual adjustment device 78. With reference to FIG. 3 and the resistance measuring circuit it may be seen that the manual adjustment device 78 controls the low voltage potential 76 of the voltage divider. Those skilled in the art will appreciate that changes at the low voltage potential inversely changes the applied voltage across the voltage divider. As the applied voltage across the voltage divider is changed, the operational range that defines the maximum values of the measured signal 88 change inversely to the value at the low voltage potential lead 76 as well. This change in the operational range affects the indicator range that defines the maximum values provided on the indicator circuit 24. In order to maintain the indicator range at a calibrated constant level in the indicator circuit 24, the feedback and control circuit adjusts the feedback gain of the second stage amplifier circuit to compensate for changes in the operational range of the measured signal 88. It will further be appreciated that when the low voltage potential 76 is adjusted to closely match the upper voltage potential 56 the voltage range within which different in resistances may be measured is very small. For such small ranges the programmable gain high circuit 46 is needed. Throughout the range of low voltage potential values, the feedback and control circuit adjusts the op-amp output by adjusting the gain at the negative input lead of the op-amp. In order to perform adjustment in the gain at the negative input lead of the op-amp and to toggle between programmable gain high and programmable gain low modes with switch 256, the feedback and control circuit includes a feedback circuit 52, a control circuit 54 and a compensation circuit 55.

The feedback circuit 52 of the feedback and control circuit 50 includes a Buf-TA lead connected to the low voltage potential lead 76 and that connects through a resistor 306 to a low resolution input lead 308 to the MCU and includes a capacitor 310 to ground to filter the signal. The output of the resistor 306 also connects to the positive input lead 312 of an op-amp 314. The negative lead 316 of the op-amp includes a gain circuit including a resistive feedback branch 318 in series with a potentiometer 324 and a capacitive branch 320 connected in parallel between the negative lead 316 and the output lead 322. The potentiometer 324 is balanced by a pair of fixed resistors 326 and 328 and a variable resistor 330 to provide the desired amplification offset. A high resolution input lead 332 connects to the output of the high resolution op-amp 314 through resistor 331.

The controller circuit 54 includes a micro-controller unit (MCU) 334 of the type model No. ST62TI0B6/SWD manufactured by SGS Thompson Electronics of Carrolton, Tex. In this particular instance the MCU 334, also commonly referred to as a central processing unit (CPU), includes a first eight bit port configured by software to receive the two output leads 308 and 332 of the feedback circuit through pins 14 and 15 respectively. These pins connect in circuit to an internal analog to digital convertor included within the MCU and which is scaled to recognize discrete changes in the input signal in the range of 0 to 255 incremental steps. The low resolution input changes continually as the manual adjustment device 78 is panned in a range of from 0.5 to 6.5, which corresponds to a range of voltage change of approximately 1.4 volts to 5.2 volts. The high resolution input is active but the voltage does not actually change until the manual adjustment device 78 is above about 4.8 volts. Below that level the high resolution input stays at about 0.7 volts (one incremental voltage drop above ground). The high resolution input range is calibrated to reach 1.00 volts as the manual adjustment device 78 reaches 5.0 and the voltage continues to increase linearly to approximately 5.2 volts when the manual adjustment device 78 rises to 6.5 volts.

The controller circuit 54 (FIG. 4C) also includes a latched activation circuit 336. The controller 54 is only needed during the period when the manual adjustment device 78 is in transition. Because this activity is intermittent, the controller 54 includes an energy saving sleep flip-flop 338. Flip-flop 338 is a set-reset flip-flop of the type model No. 4013B manufactured by Motorola. A lead 340 from the digital circuit 28 (FIG. 2) triggers a latch gate normally set to a "high" voltage 341. When the digital circuit 28 detects a change in the low potential wiper lead output 91 (FIG. 3), it changes a signal from "high" to "low" transmitted in the lead 340 to the indicator circuit 24 (FIG. 1). This lead 340 is also connected to the activation circuit 336. When the level 340 is drawn to ground or "low" flip-flop 338 changes the signal output 342 and sends an interrupt signal to the MCU which in effect "wakes-up" the MCU.

The controller circuit 54 includes power and ground leads 344 and 346 connected at pins 1, 2, 5, 6 and 20 in a conventional manner. An MCU reset interrupt circuit 348 is connected to pin 7 of the MCU. The reset switch is timed to cause a reset signal to occur at pin 7 should there be a drop in the circuit power. The reset is designed to toggle on/off as the voltage passes 4.5 volts. As the voltage rises from zero and approaches 4.5 the reset stays off. When the voltage passes above 4.5 volts the reset turns on and stays on as long as the voltage remains at or above 4.5 volts. The reset turns off if the voltage drops below 4.5 volts and stays off as long as the voltage remains below 4.5 volts. A clock 350 operating at 4 Mhz connects to pins 3 and 4 and is of the type model No. PX400 manufactured by Panasonic.

The controller 54 in response to the feedback circuit 52 and under the control of software is operative to generate a calibration signal. The calibration signal is sent through lead 356 across MCU pins 18 and 19 to the compensator circuit 55.

The compensator circuit 55 of the preferred embodiment includes a digitally controlled variable resistor 354 or digital potentiometer. The digital potentiometer 354 is of the type model No. X9C103 manufactured by Xicor of Milpitas, Calif. The digital pot 354 receives an input voltage TA_Ref 160 which provides an input signal. The output lead 357 of the variable resistance circuit, filtered for RF noise interference by a capacitor 358 connected to ground connects to the negative input 182 of the second operational amplifier 172 at 226, FIG. 4A. This lead is also illustrated as lead R+ in FIGS. 4A and 4C. The resistance of the digital pot 354 changes in response to the calibration signal from the MCU 334. The changes in the variable resistance serve to counteract the effect of predicted undesirable characteristics in the measured signal.

With reference to FIGS. 4A, B and C, the MCU 334 cooperates with the feedback circuit 52 and compensator circuit 55 under the control of software which configures the conventional MCU 334 to actively monitor the circuit to perform the calibration function. The software program includes a main routine and eleven subroutines. References to TA in the flow diagrams correspond to the manual adjustment device 78 FIG. 3. The preferred embodiment of each is described below.

Figure 5A:
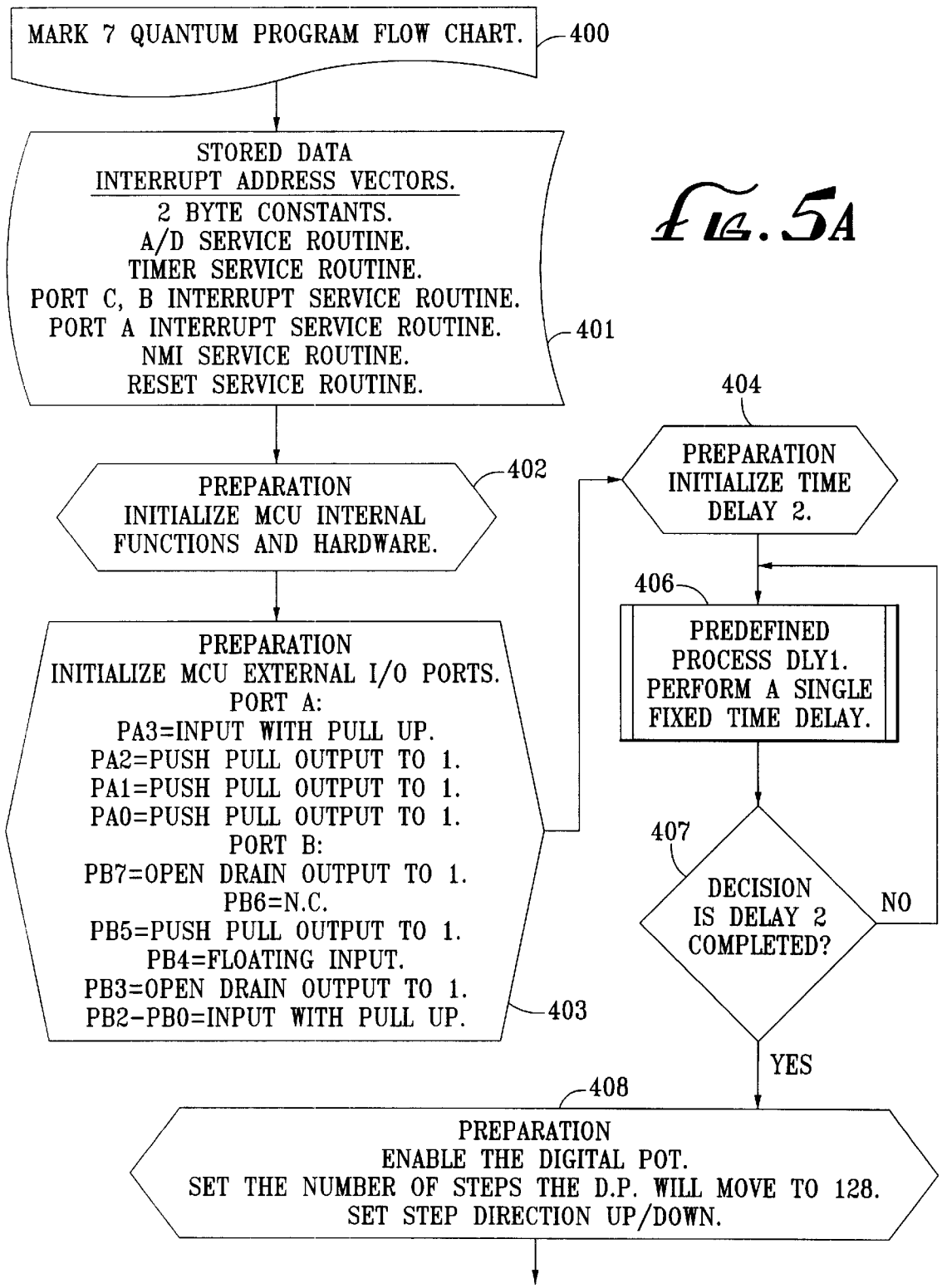
Figure 5B:
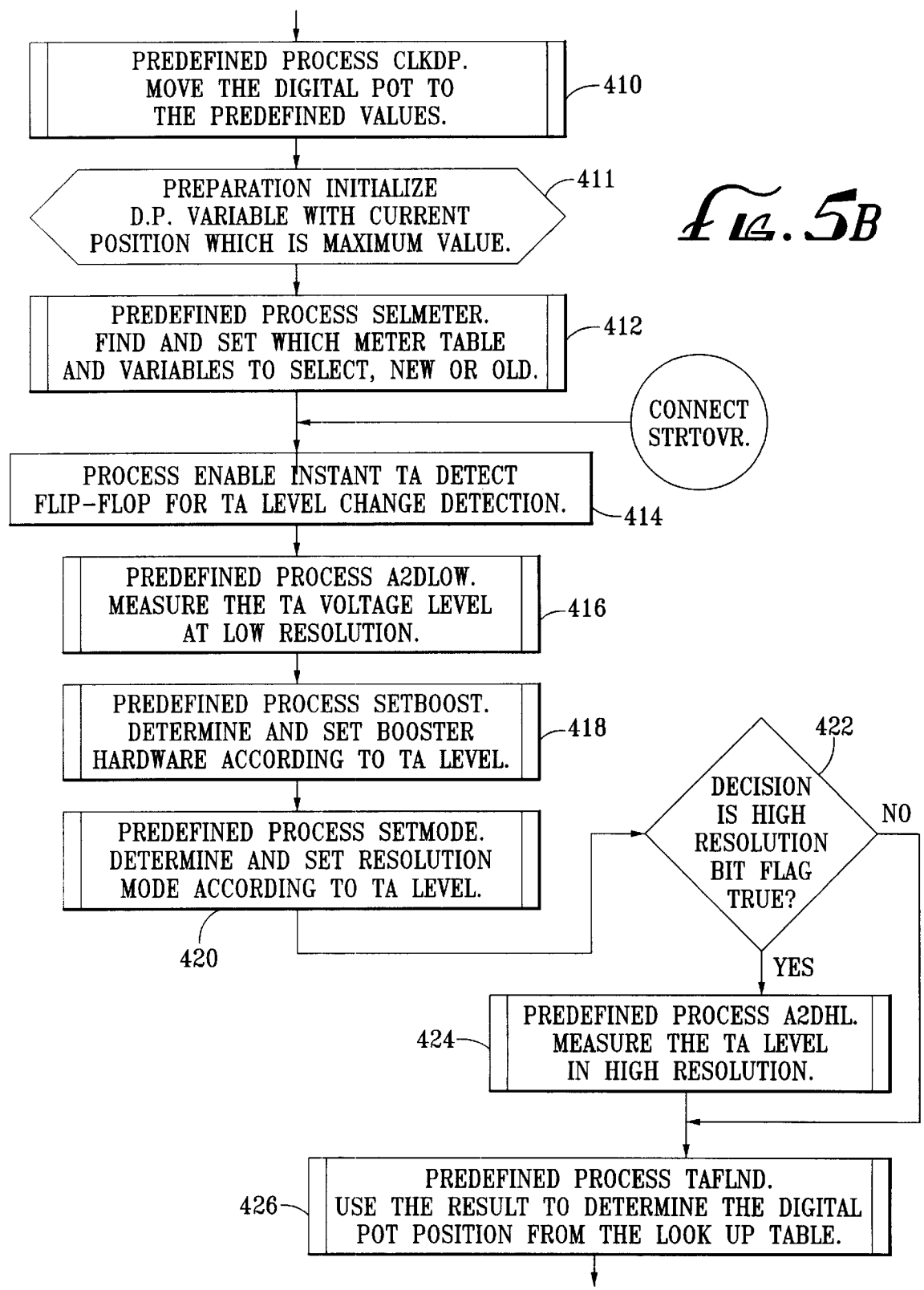
Figure 5C:
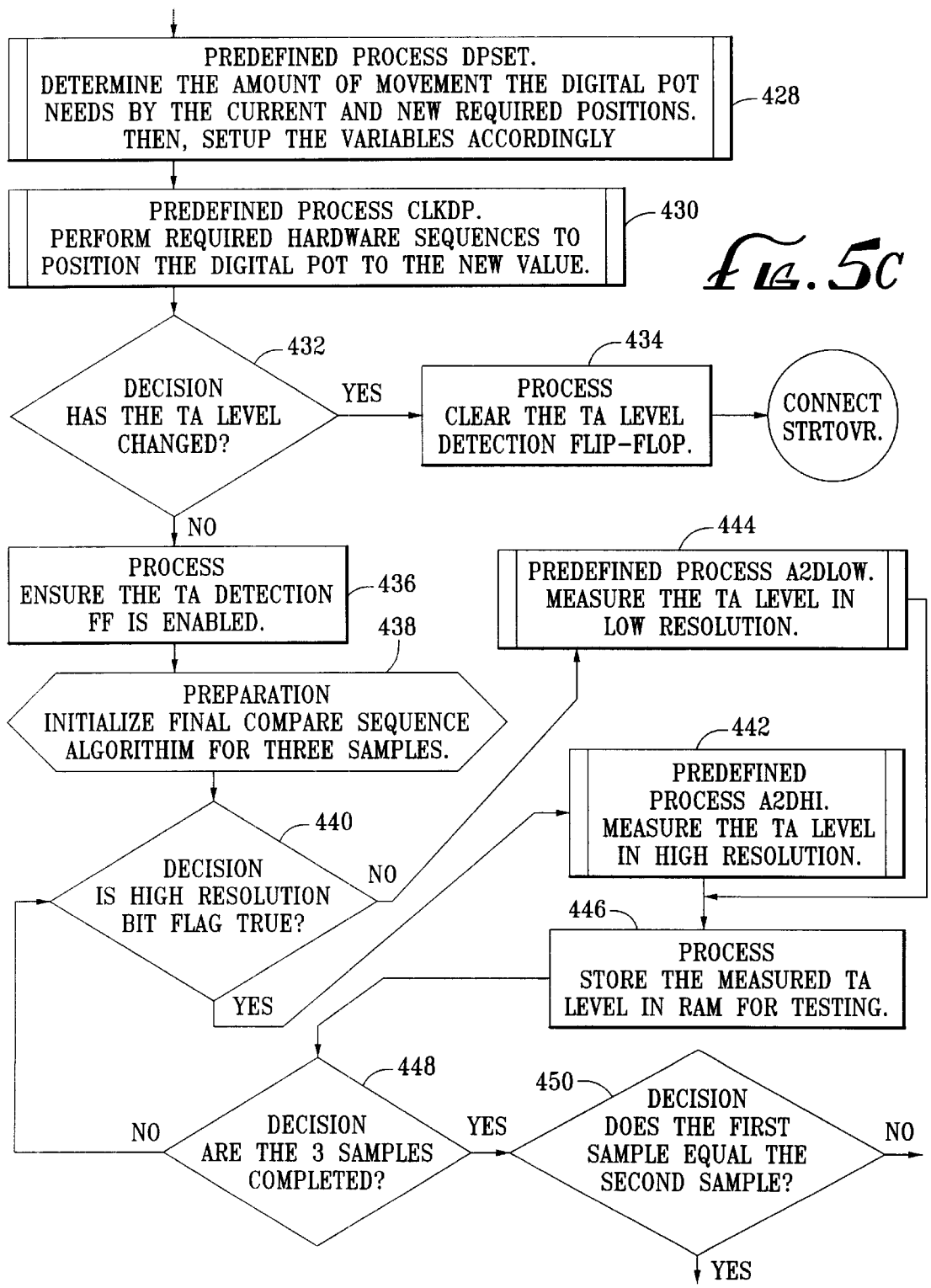
Figure 6:
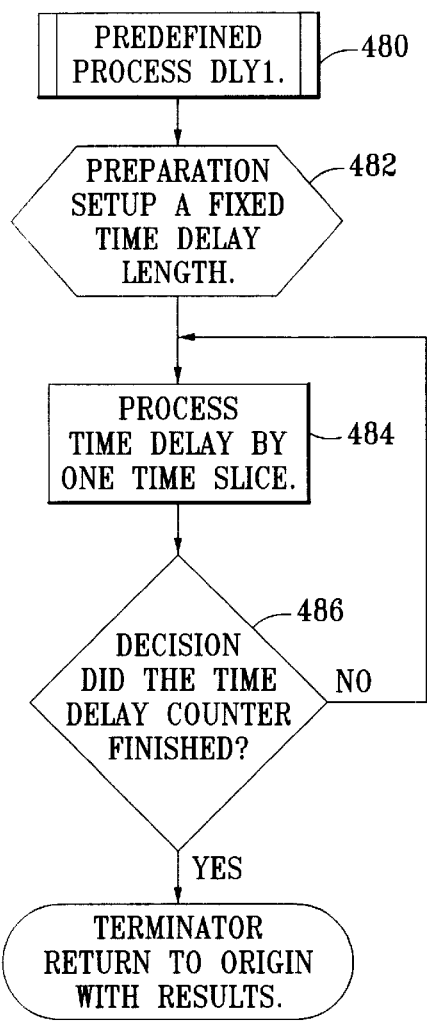
FIG. 6 represents a flow diagram of a delay routine.
Figure 7:
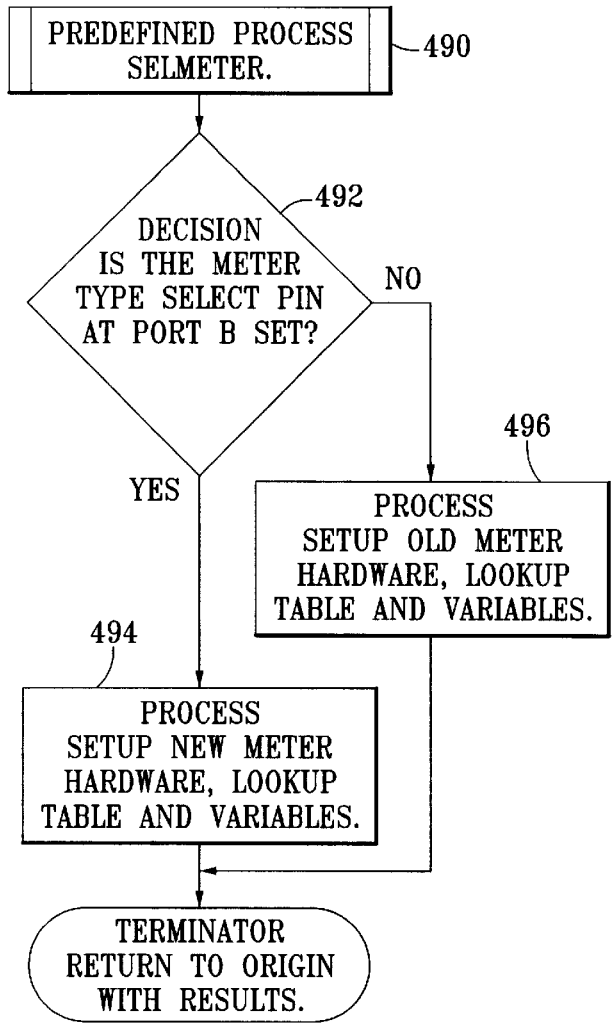
FIG. 7 represents a flow diagram of a select meter routine.
Figure 10:
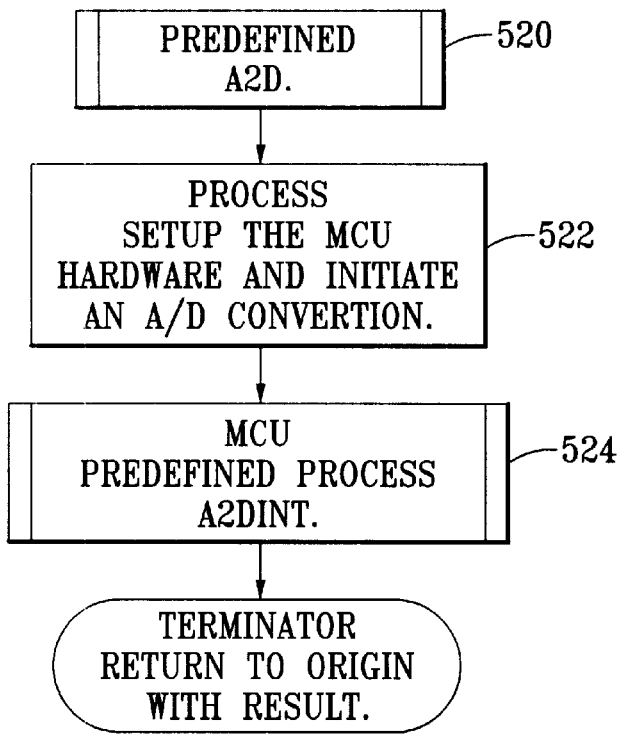
FIG. 10 represents a flow diagram of an analog-to-digital conversion routine.
Figure 11:
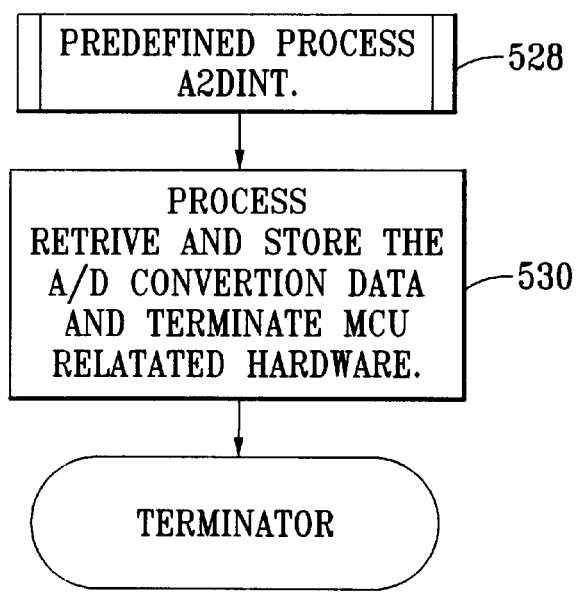
FIG. 11 represents a flow diagram of an analog-to-digital interrupt routine.
Figure 12:
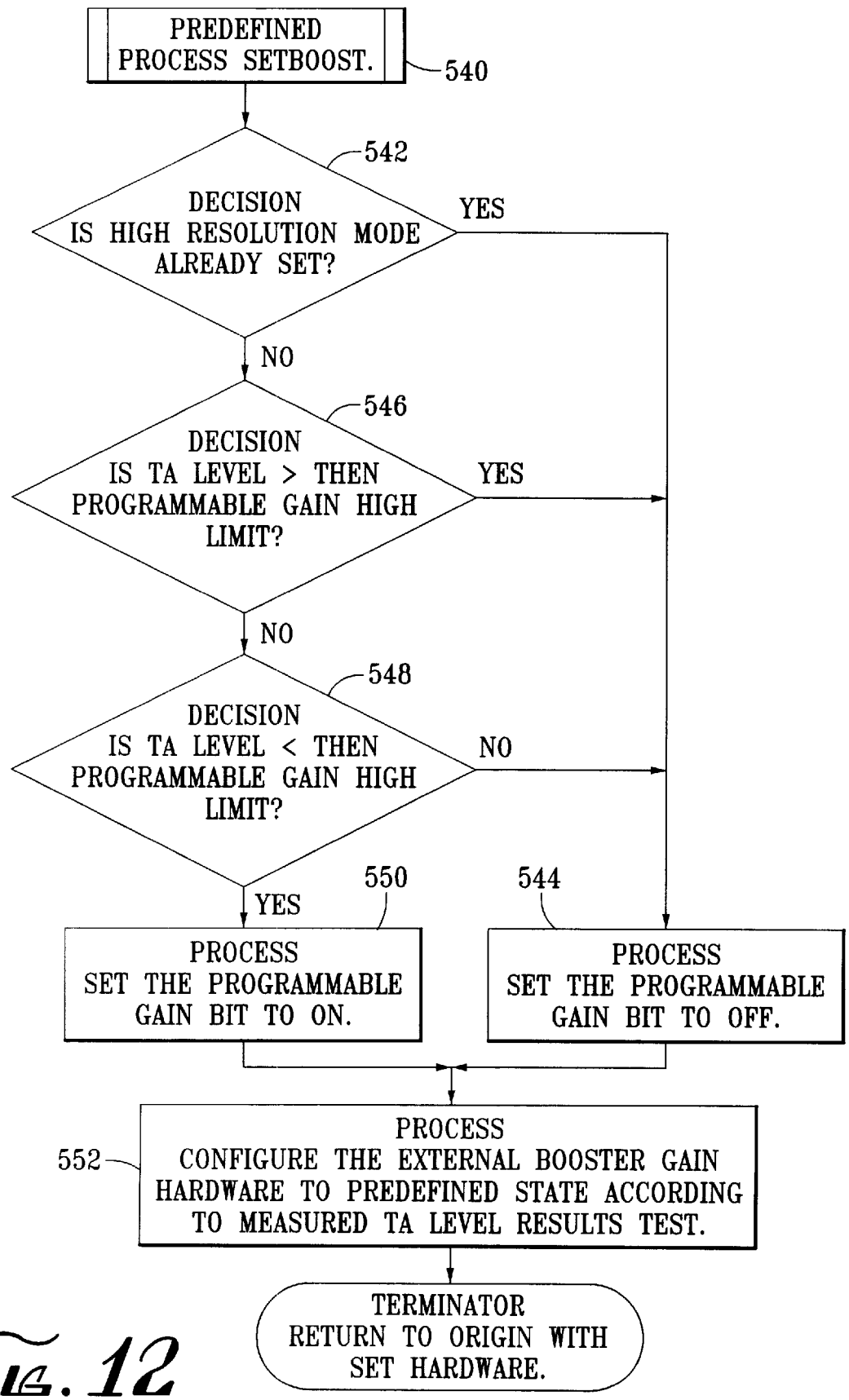
FIG. 12 represents a flow diagram of a set programmable boost routine.
Figure 13:
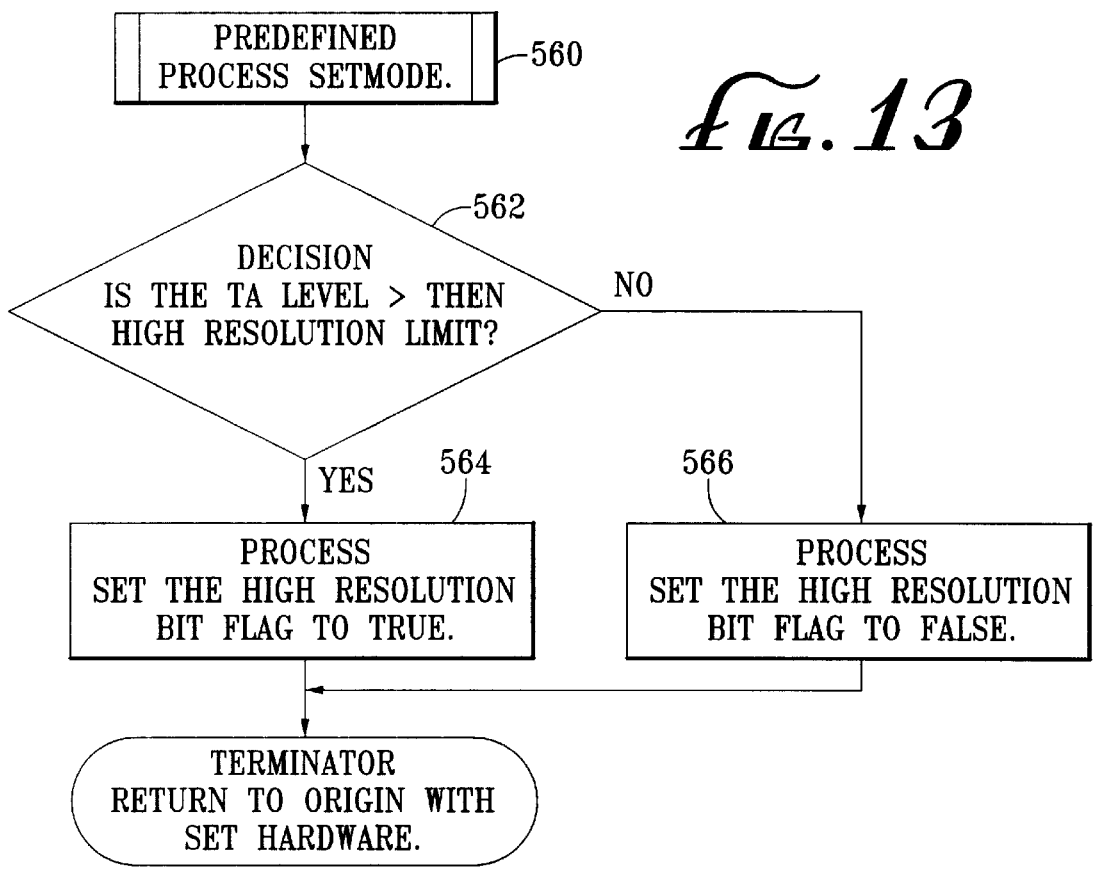
FIG. 13 represents a flow diagram of a set resolution mode routine.
Figure 14:
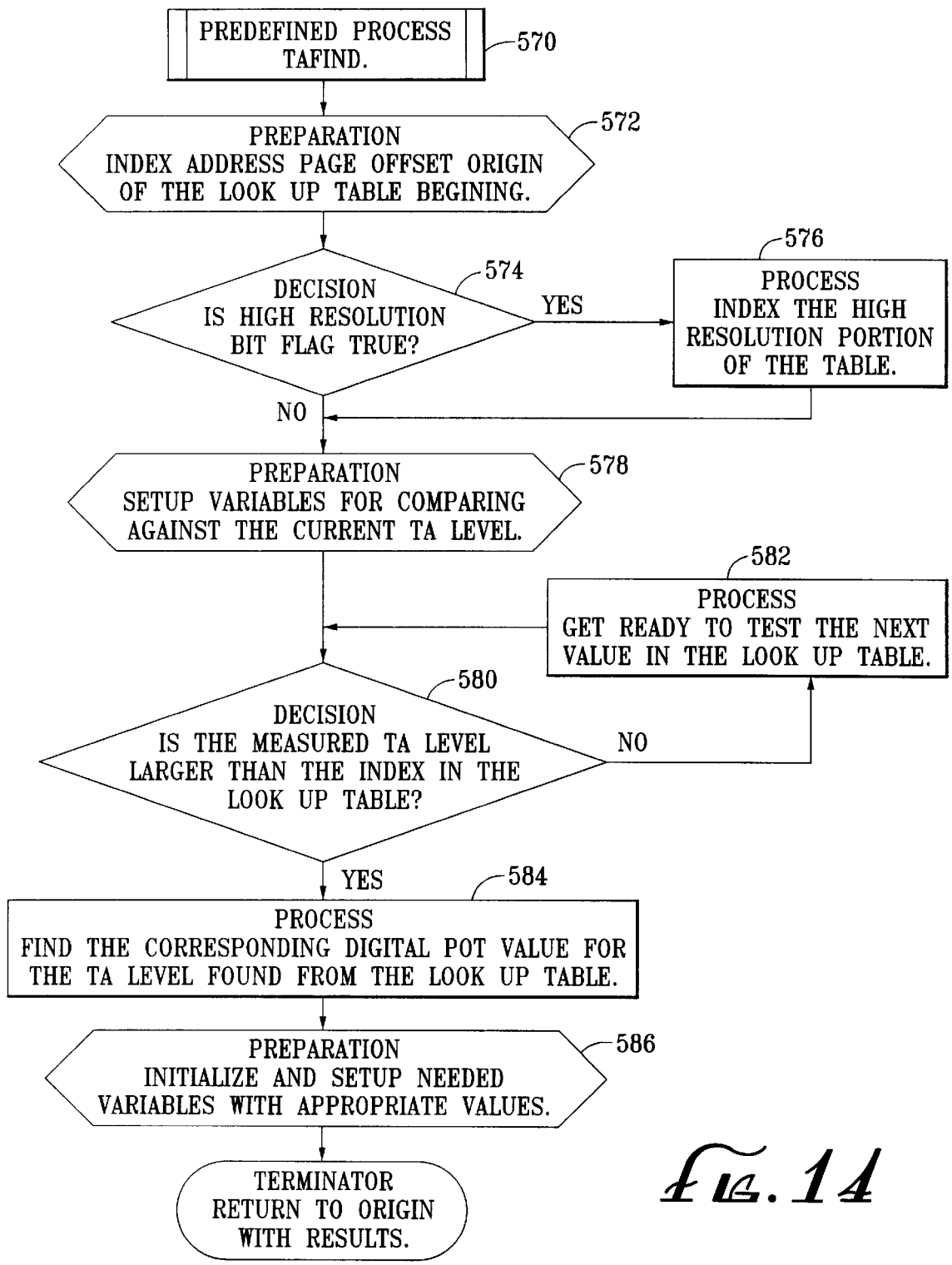
FIG. 14 represents a flow diagram of a find low voltage potential routine.
Figure 15:
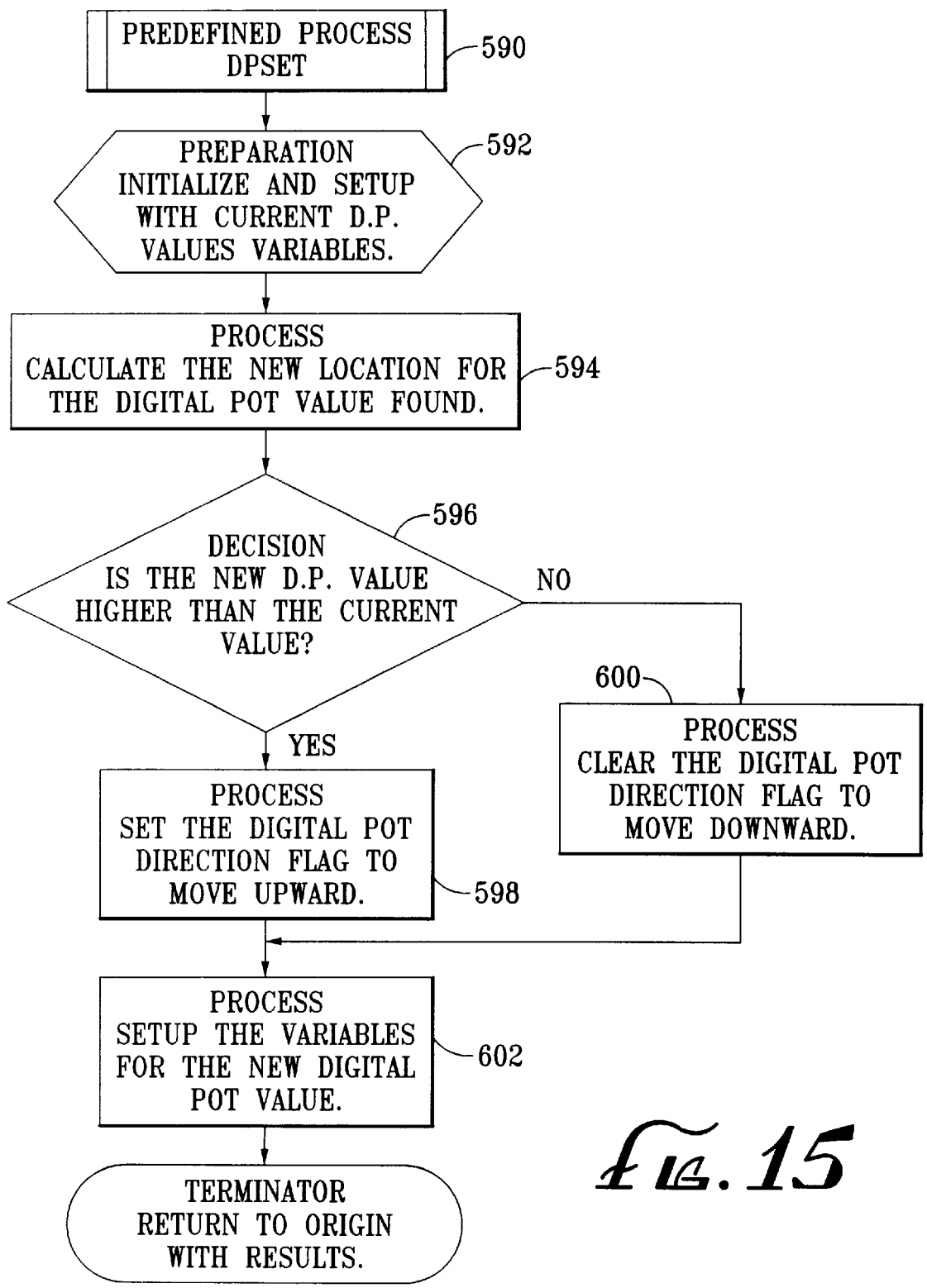
FIG. 15 represents a flow diagram for a subroutine that adjusts the digital potentiometer of a select digital resistance routine.
Figure 16:
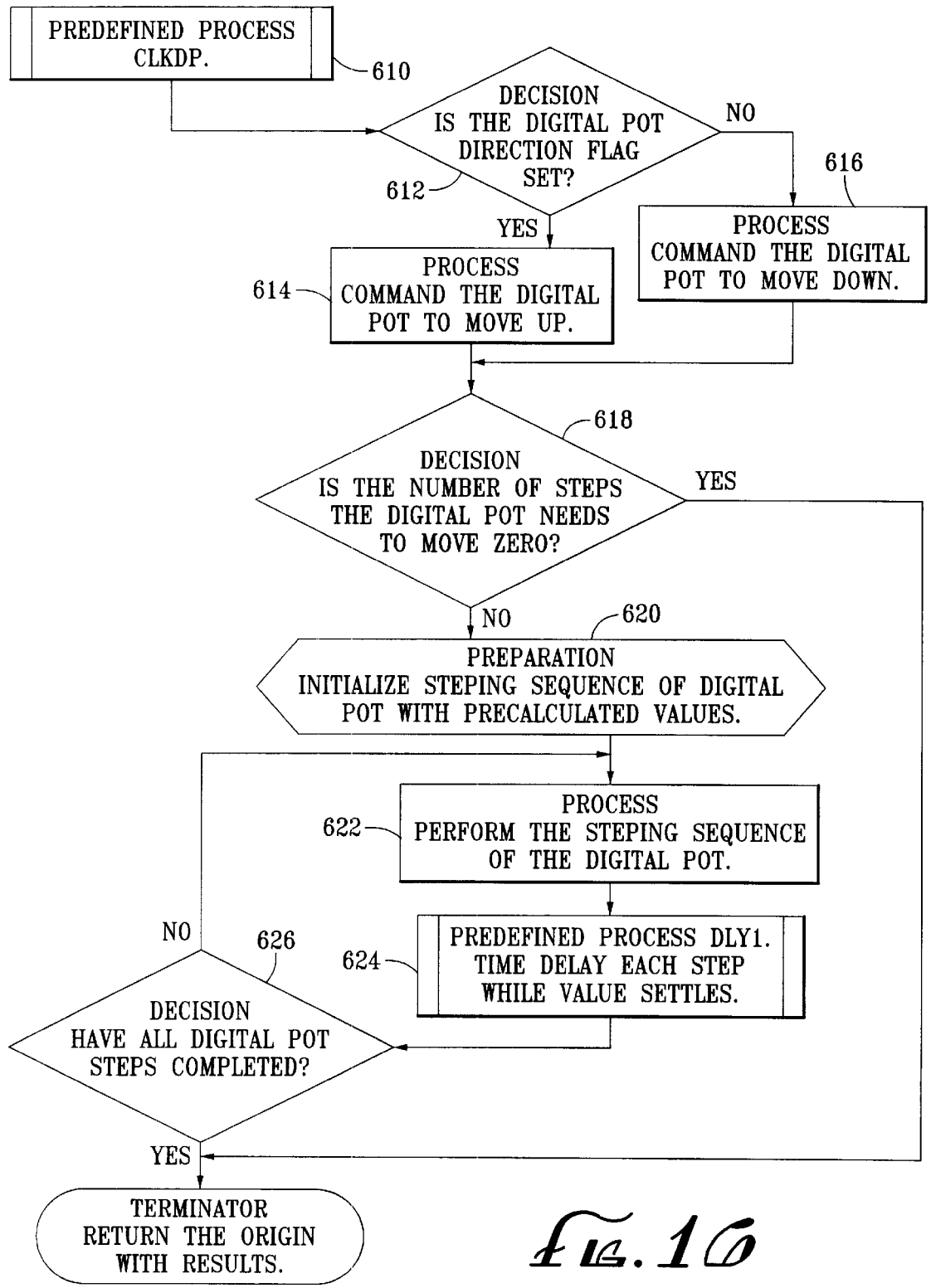
FIG. 16 represents a flow diagram for a subroutine that calibrates the digital potentiometer in response to the voltage level.

The main routine 400 (FIG. 5A–B) includes an initialization routine which includes the steps of setting up the interrupt address vectors 401 and configuring the MCU hardware and ports 402. Next a delay cycle is executed to allow for the MCU pin-leads to stabilize to their predefined levels. This cycle includes a initialize counter step 403 and do-until loop 404 which calls a delay subroutine 406 for two cycles. In the next step 408, the digital potentiometer or digital pot is set. The range of the digital pot is scaled into 100 incremental steps, and positive and negative limits are determined. Next a digital pot configuration routine (clkdp) 410 is executed to set an initial value for the digital resistor. Following the configuration routine, a meter type (selmeter) 412 subroutine is executed. Upon completion of the meter type subroutine 412, the initialization routine is completed and the active calibration mode begins.

The active calibration mode is the main subroutine performed by the MCU 334 (FIG. 4C) and repeats continuously during the time the MCU is active. First, the sleep flip-flop is configured to detect a TA level change in an enable TA detect step 414. Next, a measure TA potentiometer at low level resolution subroutine (a2d low) 416 is called. A set boost subroutine (setboost) 418 determines and configures the booster gates for high or low programmable gain. A set mode subroutine (setmode) 420 then determines and sets the resolution mode internally to "high" or "low" resolution. Next, the resolution mode is checked in a check resolution step 422. If the resolution flag bit is high, a measure TA in high resolution subroutine (a2dhigh) 424 is called. Otherwise, no measurement is made. In the next step a find TA subroutine (TA find) 426 determines the TA value. Next, a digital pot set subroutine (dpset) 428 determines amount of calibration needed. Next, the clkdp routine 430 is called to reconfigure the digital pot to the desired new calibration position. Following calibration of the compensator, a check change in TA level, step 432, is performed. If a change in the TA pot occurred, the sleep Flip-Flop is cleared in step 434, and the main program returns to the TA enable 414 step. Otherwise, the main program continues with a reconfigure flip-flop step 436 to ensure the flip-flop is properly configured.

Next, a counter register is configured at step 438 for a three sample do-loop. A check for high resolution, step 440, if high detected, calls a measure TA in high resolution subroutine 442. Otherwise, the measure TA in low resolution subroutine 444 is called. The next step 446 stores the measured sample in memory. A decrement sample counter and check for end of sampling step 448 returns to the check resolution step, if there are less than three samples. Otherwise, the program initiates testing of the sampled data. The purpose of testing is to determine whether the operator has completed the adjustment of the manual adjustment device to a new position. The MCU recognizes that the operator has completed rotation of the device and the measurement is now stable when any two of the three data samples are equal. While other steps and other data samples may be performed to determine whether an operator has completed adjustment of the manual adjustment device, the preferred embodiment includes three data condition steps 450, 452 and 454. In a first testing step 450, the first data sample is compared to the second data sample. If the first and second data samples are equal, testing stops and the program continues to a check TA status step 456. Otherwise, testing continues with a second testing step 452 that compares the first data sample to the third data sample. If the first and third samples are equal, testing stops and the program continues to the check TA status step 456. Otherwise testing continues with a third testing step 454 that compares the second data sample with the third data sample. If the second and third data samples are equal the program continues to the check TA status step 456. Otherwise, the TA is still being adjusted and the program returns to the beginning of the calibration routine at the TA enable step 414.

If any of the data samples are equal indicating that manual adjustment has been completed and valid data is present, the check TA status step 456 is performed to determine whether the manual adjustment device has moved since sampling by checking the TA flip-flop. If the flip-flop has been triggered, the flip-flop is cleared and reset at step 458 and the program returns to the TA enable step 414. Otherwise, the compensator is calibrated again in the sequence listed: the a2d low 416, setboost subroutine 460, tafind subroutine 462 dpset subroutine 464, and clkdp subroutine 466. Next, the TA flip-flop is checked again for movement 468. If movement, the TA flip-flop is cleared 470 and the program returns to the TA enable step 414. Otherwise, the program enters sleep mode 472 to conserve power and inhibit noise. An active part of the MCU hardware monitors the input signal from the TA flip-flop. If an interrupt is received, the MCU wakes-up at step 474, and returns to the check for TA movement step 468. Thus, the main program maintains calibration of the amplifier circuit.

The sleep mode was found to be useful, because the MCU 334 would otherwise continuously calibrate the amplifier circuit. This resulted in periodic jumps in the indicating circuit output which was unrelated to the resistance measuring circuit. The sleep mode eliminated the random jumps and stabilized the compensator circuit by putting the controller circuit to sleep during stable periods.

As discussed above in regard to the main routine, subroutines perform specific tasks within the main routine. These subroutines will be described in the order that they are called in the main program.

The delay (dly 1) subroutine 480 includes a counter constant load step 482 for a do-loop, a counter decrement step 484, and a check for end of loop step 486. Upon completing the loop for the required number of cycles the subroutine returns to the program that called it.

The select meter (selmeter) 490 subroutine is called in the initialization part of the main program. The present feedback and control circuit of the present invention can be executed on any of the preexisting E-meters using a voltage divider or resistance bridge of the types described earlier and incorporated by reference. The circuit and software of the present invention can be configured to work with either a voltage divider circuit as illustrated in the preferred embodiment or a resistance bridge circuit. The select meter subroutine checks a port pin on the MCU. This pin is either drawn to a "high" or "low" voltage depending upon the type of resistance measuring circuit used. The select meter subroutine 490 includes a check pin step 492. If the pin is "high" an initialize step 494 for the voltage divider circuit is performed, otherwise an initialize step 496 for the resistance bridge circuit is performed. Upon completing either initialization step, the program returns to the main program.

The a2dlow subroutine 500 measures the TA level in a low resolution mode. The subroutine includes a initialize step 502 to set the MCU's internal analog to digital convertor for low resolution mode. Next an analog to digital convertor (a2d) subroutine is called step 504. Upon return, the analog to digital convertor is reset, step 506 and the subroutine returns to the program that called it.

The a2dhigh subroutine 510 measures the TA level in High resolution mode. The subroutine includes an initialize step 512 to set the MCU's internal analog to digital convertor for high resolution mode. Next the a2d subroutine is called 514. Upon return, the analog to digital convertor is reset 516 and the subroutine returns to the program that called it.

The use of high and low resolution modes allow for the 8-bit internal analog to digital convertor to operate in effect as a 12 bit analog to digital convertor, which is required for the entire voltage range of 0–5.2 volts where low resolution is in the range of 1–4.8 volts and high resolution is in the range of 4.8–5.2 volts. In low resolution mode the A to D converter senses the TA wiper voltage directly so that the voltage range of 1.4 volts to 5.2 volts corresponds to decimal values of approximately 67 through 255. In high resolution mode the A to D converter sees an input range of 1.0 volts to 5.2 volts, which corresponds approximately to the range of 4.8 volts to 5.2 volts at the TA wiper, which in turn corresponds to decimal values of 49 through 255.

The a2d subroutine 520 in a measured analog signal step 522 converts the analog signal measured at pin 14 of the MCU to a digital value when called by the a2dlow subroutine, step 500, and converts the analog signal measured at pin 15 of the MCU to a digital value when called by the a2dhigh, step 510, subroutine. The a2d subroutine 520 then enters a wait mode to allow for the MCU analog to digital convertor to complete the conversion. Upon completion of the conversion, the MCU generates an interrupt 524 that includes an address vector to a a2dint subroutine 528. The a2dint subroutine 528 retrieves and stores the analog to digital data and terminates the related hardware 530. The a2dint subroutine returns to the a2d subroutine and in turn the a2d subroutine returns to the subroutine that called it.

The set booster subroutine 540 switches the booster resistor in the variable resistance circuit between the programmable gain high and low portions of the variable resistor circuit. The set booster subroutine includes testing the voltage potential to determine whether the TA analog to digital setting is in high resolution mode or low resolution mode. If high resolution mode is set, step 542, then the program jumps to a programmable high gain active step 544. Otherwise additional testing occurs. In this case, a compare TA level to a programmable gain low limit step 546 jumps to the programmable gain high active step 544 if the TA level is greater than the programmable gain low limit. Otherwise additional testing is performed. In this case, a compare TA level to a programmable gain high limit step 548 jumps to the programmable gain low active step 550 if the TA level is less than the programmable gain high limit. Otherwise, the program goes to a programmable gain high active step 544. For either the programmable gain high active step 544 or the programmable gain low active step 550, the subroutine configures the programmable gain latch lead 552 to the corresponding high or low setting. The setboost routine then returns to the program that called.

In the presently preferred embodiment the programmable gain low limit value is less than the programmable gain high limit value. Those skilled in the art will appreciate that the flow diagram described would not require a comparison to the programmable gain high value in such instances, because the TA level for this test will always be less than the programmable gain high limit. However, in an alternate embodiment, the programmable gain high limit is less than the programmable gain low limit. This setting causes a hysteresis function to occur in switching between settings. This is useful in preventing unwanted jumps in the readout of the indicator circuit.

The setmode subroutine 560 sets the analog to digital convertor mode to either high resolution or low resolution mode. The subroutine includes a compare TA level to high resolution limit 562. The program sets the high resolution bit flag to high or logic true 564, if the TA level is greater than the high resolution limit. Otherwise the program sets high resolution bit to low or false 566. After setting the high resolution bit flag, the program returns to the program that called it.

The tafind subroutine 570 uses the TA level to determine the calibration required to eliminate any undesired characteristics in the signals output from the resistance measuring circuit. In the presently preferred embodiment, the active calibration senses the TA level to detect changes in the TA setting. In the case of the voltage divider the program voltage range from which the change in resistance may be measured decreases in direct relation to increases in the TA buffered voltage level. When the TA level becomes greater than or exceeds the preferred TA ohm range of 5 k to 12.5 k ohms, the amplitude of the signal representative of changes in the resistance of a living body correspondingly and undesirably decreases. The tafind subroutine overcomes this problem by determining an adjustment level in the variable resistance circuit to compensate for these changes using look up tables to correspondingly adjust the feedback in the amplifier circuit to compensate the change in the TA voltage and maintain the measured signal calibration. The tafind subroutine 570 includes set-up step 572 that locates the correct look up table for either the voltage divider type or resistance bridge type resistance measuring circuit. Next a check for high resolution step 574 checks whether the device is in high or low resolution. If in high resolution, the portion of the look-up table for high resolution is located in memory step 576. Next the MCU loads the TA level and look up table values into memory in a preparation step 578. The TA level is then tested in a check TA step 580 against the TA index value. The table values are read by the MCU in lowest to highest order. If the TA level is less then the index, the next TA index value is loaded 582 and the routine returns to the test step 580. Otherwise, the corresponding digital pot value is loaded in a look up step 584. Then a change digital pot set up step 586 loads the values needed to change the resistance in the digital pot. The subroutine then returns to the program that called it.

The dpset subroutine 590 configures the MCU to adjust the digital potentiometer. The subroutine 590 includes a load register step 592, a calculate new location step 594, and a check step 596 to determine whether the new value is higher or lower. If the value is higher a set direction flag step 598 to move upward is performed, otherwise a set direction flag step 600 to move downward is performed. Next, the values are loaded to begin calibration of the digital pot 602. The subroutine then returns to the program that called it.

The clkdp subroutine 610 calibrates the digital potentiometer in response to the voltage level measured from the TA potentiometer. The subroutine includes a check direction flag step 612. If the flag is high the digital pot is signaled to count upward 614. If the flag is low the digital pot is signaled to count downward 616. Next a check for no movement 618 is made. If the change is zero, the subroutine returns to the program that called it. Otherwise, the digital pot is initialized 620 to begin changing the variable resistance. The digital pot is signaled to incrementally change by one unit the direction determined during the check direction step. The incremental change is 100 ohms using the preferred digital pot. Next the delay subroutine 624 is called to allow for the signal to be received and processed by the digital pot. Then the counter is decremented and checked 626. If the counter is greater than zero the program returns to signaling step 622 and advances the digital pot another incremental step. Upon the counter reaching zero the program terminates and returns to the program step that called it.

It will be appreciated from the above disclosure that the present invention may be used to actively calibrate the amplifier to any known predetermined undesirable characteristic. This can be achieved once the characteristic has been identified and if the characteristic correspond to a measurable change in the internal signals. The microprocessor contains "lookup tables" of gain compensation factors stored in memory which were derived empirically by measuring the amplitude of a given resistance change for each point chosen of overall input resistance. Based on these compensation factors the needed gains and their corresponding feedback resistances may be calculated, thereby establishing a table of low-voltage (76) potentials vs. gain resistances established in the variable resistance 42.

In operation the device is initialized by adjusting the trim control 60 (FIG. 3), booster switch circuit 48 (FIG. 4B) and sensitivity control (not shown) such that the low voltage potential 76 (FIG. 3) is balanced for the 5K ohm meter check resistance 68. A living body is then connected across the external leads 64 and 66 of the resistance measuring circuit. In order to balance the circuit according to the overall resistance of the living body, the manual adjustment device 78 is moved until the low voltage potential 76 achieves a balance with the overall resistance in the living body. During the time that the low voltage potential 76 is being changed to achieve a balance with the overall resistance in the living body, the feedback circuit 52 (FIGS. 2 and 4C) provides the changes in the low voltage potential 76 to the control circuit 54. The control circuit 54, normally in sleep mode, awakens to the movement of the manual control device 78 as signaled by the digital circuit 28. The control circuit 54 monitors the movement of the manual control device 78 until the adjustment has been completed. Upon completion of adjustment, the control circuit 54 determines the gain adjustment value using the look-up table and signals the compensator circuit 56 to adjust the gain of the amplifier circuit. The gain is adjusted to eliminate the undesirable characteristic of the sensitivity decreasing in response to increases in the low voltage potential 76. The gain is adjusted automatically such that the sensitivity is maintained at a constant level independent of changes in the low voltage potential 76.

In an alternate embodiment of the calibration circuit, a voltage controlled operational amplifier is included in the amplifier circuit (not shown). In this embodiment, the low voltage potential 76 is connected to the control voltage input of the amplifier. The amplifier may be placed with a negative input lead and output lead in series at the output lead corresponding to lead 130 (FIG. 4A) of the voltage follower. The positive input lead would be connected to a constant high voltage source. This operational amplifier calibrates the gain of the amplifier in proportion to changes in the low voltage potential. An operational amplifier of the type suitable for this purpose is Model No. VCA610 manufactured Burr Brown of Tucson, Ariz.

In a second alternative embodiment of the calibration circuit the manual adjustment device 78 may include a conventional dual ganged pot in which a second resistor may be incrementally adjusted at a nonlinear, inverse resistance to the variable resistor 82 value (FIG. 3). The second pot would connect between the reference voltage (FIG. 4C) and the negative input lead of the second operational amplifier circuit (FIG. 4B).

Another embodiment in which the radio frequency interference may be reduced further includes a radio frequency insulating paint coated on the interior surface of a housing for the present invention. A paint suitable for this purpose is manufactured by Sandstrom Products Co., Port Byron, Ill. and sold as Model Sanpro A405 also known as silverling EMI/RFI shield coating paint.

While the present invention has been described in connection with what are presently considered to be the most practical, and preferred embodiments, it is to be understood that the invention is not to be limited to the disclosed embodiments, but to the contrary, is intended to cover various modifications and equivalent arrangements included within the spirit of the invention, which are set forth in the appended claims, and which scope is to be accorded the broadest interpretation so as to encompass all such modifications and equivalent structures.

What is claimed is:

1. A device for indicating changes in the resistance of a living body comprising:

a resistance measuring circuit having external leads, and adapted to measure resistances within a first range of relatively low variable resistances, to measure resistances within a second range of relatively high variable resistances across a living body and to produce a measured signal;

an amplifier circuit connected to the resistance measuring circuit and adapted to amplify the measured signal to a perceptible level;

an indicator circuit connected to said amplifier circuit and adapted to produce the measured signal in a perceptible form; and a sensitivity adjustment circuit means connected to said amplifier circuit, connected to said indicator circuit and for automatically increasing sensitivity of said indicator circuit for a high variable resistance in said second range measured in said resistance measuring circuit.

2. The device for indicating changes in the resistance of a living body of claim 1:

wherein said sensitivity adjustment circuit means is also for automatically adjusting sensitivity of said indicator circuit for a low variable resistance in said first range measured in said resistance measuring circuit.

3. The device for indicating changes in the resistance of a living body of claim 1 wherein:

said sensitivity adjustment circuit means includes a control circuit.

4. A device for indicating changes in the resistance of a living body comprising:

a resistance measuring circuit having external leads;

an amplifier, circuit connected to the resistance measuring circuit;

an indicator circuit connected to said amplifier circuit;

a sensitivity adjustment circuit connected to said amplifier circuit, said indicator circuit capable of automatically increasing sensitivity of said indicator circuit for a high variable resistance setting in said resistance measuring circuit; and said sensitivity adjustment circuit includes a dual ganged potentiometer.

5. The device for indicating changes in the resistance of a living body of claim 1 wherein:

said sensitivity adjustment circuit means includes a voltage controlled operational amplifier.

6. A device for indicating changes in the resistance of a living body comprising:

a resistance measuring circuit having external leads and a manual adjustment potentiometer;

an amplifier circuit connected to the resistance measuring circuit;

an indicator circuit connected to said amplifier circuit;

said amplifier circuit including a calibration circuit operative to automatically adjust the gain of said amplifier circuit in response to movement of said adjustment potentiometer.

7. The device for indicating changes in the resistance of a living body of claim 6 wherein said calibration circuit includes:

a measured input feedback circuit responsively connected to said resistance measuring circuit;

a compensation valve control circuit responsively connected to said feedback circuit; and a constant amplitude response compensator circuit connected to and responsive to said control circuit.

8. The device for measuring and indicating changes in the resistance of living body of claim 6 wherein said calibration circuit includes a feedback circuit adapted to receive signals representative of the overall resistance of a living body.

9. The device for measuring and indicating changes in the resistance of living a body of claim 8 further including control circuit connected to said feedback circuit and adopted to determine from said input signal a compensation signal corresponding to a change in the gain of the amplifier circuit.

10. The device for measuring and indicating changes in the resistance of a living body of claim 9 further including a compensator circuit adapted to receive said compensation signal and to adjust said amplifier circuit to maintain a generally constant amplitude response.

11. A device for indicating changes in the resistance of a living body comprising:

a resistance measuring circuit having leads extending therefrom;

an amplifier circuit having leads extending therefrom;

an indicator circuit having leads extending therefrom;

a plurality of manually controlled devices having leads extending therefrom;

at least one lead extending from each of said circuits and from each of said manually controlled devices; and at least one inductor included within said resistance measuring circuit; and within said amplifier circuit whereby radio interference conducted through said circuits is reduced.

12. A device for indicating changes in the resistance of a living body comprising:

a resistance measuring circuit;

an amplifier circuit;

an indicator circuit;

a housing surrounding said resistance measuring circuit, said amplifier circuit and said indicator circuit; and a radio frequency insulating paint coating said housing.

13. A method for maintaining a generally constant amplitude response to a predetermined measured input in a device for measuring changes in the resistance of a living body, the device having a resistance measuring circuit, an amplifier circuit and an indicator circuit, comprising:

initializing said resistance measuring circuit and said amplifier circuit;

connecting a living body to said resistance measuring circuit;

establishing the overall resistance in the living body; and adjusting the gain of said amplifier circuit according to a predetermined ratio such that a generally constant amplitude response is generated for a measured change in resistance.

14. The device of claim 6 further including a computer interface adapted to provide a simulated measured signal.

15. The device of claim 6 wherein said amplifier circuit includes an op-amp having a capacitor connected in circuit between positive and negative inputs to said op-amp.

16. The device of claim 7 wherein said control circuit further includes:

a microcontroller connected to said feedback circuit; and an analog to digital converter connected to said feedback circuit.

17. The device of claim 7 wherein said control circuit further includes:

an activation circuit adapted to activate said control circuit upon transition of said manual adjustment potentiometer.

18. The device of claim 7 further including;

a microcontroller in said control circuit and which is connected to said feedback circuit; and computer-implemented software operatively controlling said microcontroller.

19. The device of claim 18 further including a calibration input signal compensator circuit and a digital potentiometer connected to said amplifier circuit.

20. The device of claim 6 further including:

a microcontroller in said calibration circuit;

computer-implemented software adapted to configure said calibration circuit, to continuously detect changes in the manual adjustment potentiometer, and to determine and set a resolution mode from a set of predetermined resolution modes.

21. The method of claim 13 further including:

manually adjusting a potentiometer as part of establishing the overall resistance; and setting a resolution mode for establishing overall resistance of the living body to one of a plurality of predetermined resolution modes.

22. The method of claim 21 further adjusting the gain of said amplifier circuit by matching predetermined compensation factor signals to predetermined resistance change values corresponding to changes in the overall resistance in the living body.

* * * * *